United States Patent
Bonutti et al.

(10) Patent No.: US 6,468,293 B2
(45) Date of Patent: Oct. 22, 2002

(54) METHOD AND APPARATUS FOR SECURING A SUTURE

(76) Inventors: Peter M. Bonutti, 1303 W. Evergreen Plz., Effingham, IL (US) 62401; Matthew J. Cremens, Box 1, Rte. 2, Effingham, IL (US) 62401; Ping Liu, 2201 Oakwood Pl., Charleston, IL (US) 61920

( * ) Notice: Subject to any disclaimer, the term of this patent is extended or adjusted under 35 U.S.C. 154(b) by 0 days.

(21) Appl. No.: 09/850,287

(22) Filed: May 7, 2001

(65) Prior Publication Data

US 2001/0021862 A1 Sep. 13, 2001

Related U.S. Application Data

(62) Division of application No. 09/429,100, filed on Oct. 28, 1999, now Pat. No. 6,231,592, which is a division of application No. 08/905,084, filed on Aug. 1, 1997, now Pat. No. 6,010,525.

(51) Int. Cl.$^7$ ................................................ A61B 17/04
(52) U.S. Cl. ..................................... 606/232; 606/148
(58) Field of Search ................................. 606/232, 233, 606/148, 151, 220, 75; 623/16; 128/898

(56) References Cited

U.S. PATENT DOCUMENTS

| | | |
|---|---|---|
| 3,513,848 A | 5/1970 | Winston |
| 4,662,068 A | 5/1987 | Polonsky |
| 4,750,492 A | 6/1988 | Jacobs |
| 4,935,028 A | 6/1990 | Drews |
| 5,306,280 A | 4/1994 | Bregen et al. |
| 5,366,480 A | 11/1994 | Corriveau et al. |
| 5,376,126 A | 12/1994 | Lin |
| 5,383,905 A | 1/1995 | Golds et al. |
| 5,527,341 A | 6/1996 | Gogolewski et al. |
| 5,593,425 A | 1/1997 | Bonutti et al. |
| 5,630,824 A | 5/1997 | Hart |
| 5,643,295 A | 7/1997 | Yoon |
| 5,645,553 A | 7/1997 | Kolesa et al. |
| 5,665,109 A | 9/1997 | Yoon |
| 5,669,917 A | 9/1997 | Sauer et al. |
| 5,690,654 A | * 11/1997 | Ovil ............................ 606/148 |
| 5,720,747 A | 2/1998 | Burke |
| 5,725,556 A | 3/1998 | Moser et al. |
| 5,735,875 A | 4/1998 | Bonutti et al. |
| 5,735,877 A | 4/1998 | Pagedas |
| 5,769,894 A | 6/1998 | Ferragamo |
| 5,810,849 A | * 9/1998 | Kontos ....................... 606/144 |
| 5,810,853 A | 9/1998 | Yoon |
| 5,845,645 A | 12/1998 | Bonutti |
| 5,921,986 A | 7/1999 | Bonutti |
| 5,951,590 A | 9/1999 | Goldfarb |
| 6,045,551 A | 4/2000 | Bonutti |

FOREIGN PATENT DOCUMENTS

JP 8-140981 6/1996

* cited by examiner

*Primary Examiner*—Kevin T. Truong
(74) *Attorney, Agent, or Firm*—Tarolli, Sundheim, Covell, Tummino & Szabo L.L.P.

(57) ABSTRACT

Improved method is provided to secure a suture relative to body tissue. A suture retainer is moved along first and second sections of a suture toward the body tissue. When a predetermined minimum force is being transmitted between the suture retainer and the body tissue, the first and second sections of the suture are gripped with the suture retainer by plastically deforming material of the suture retainer. The material of the suture retainer cold flows under the influence of force applied against the surface areas on the suture retainer. One or more bends are formed in each of the sections of the suture to increase the holding action between the suture retainer and the sections of the suture. The bends may be formed by wrapping a turn of the suture around a portion of the suture retainer. During movement of the suture retainer toward the body tissue, the bends are moved along the first and second sections of the suture.

32 Claims, 12 Drawing Sheets

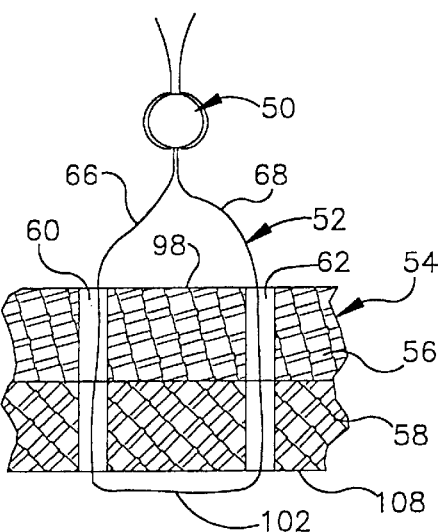
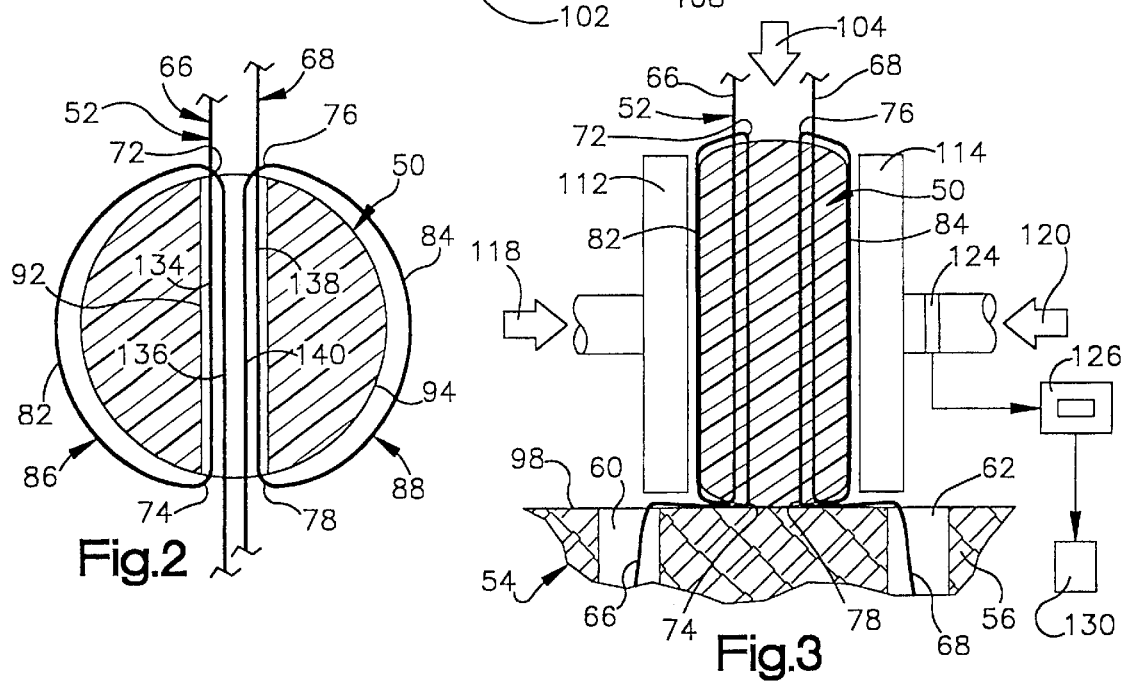
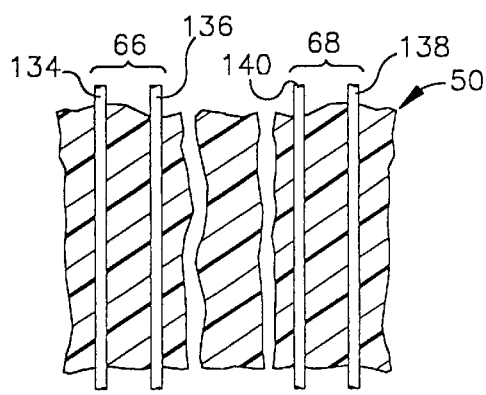
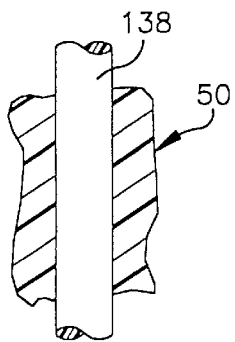
Fig.1
Fig.2
Fig.3
Fig.4
Fig.5

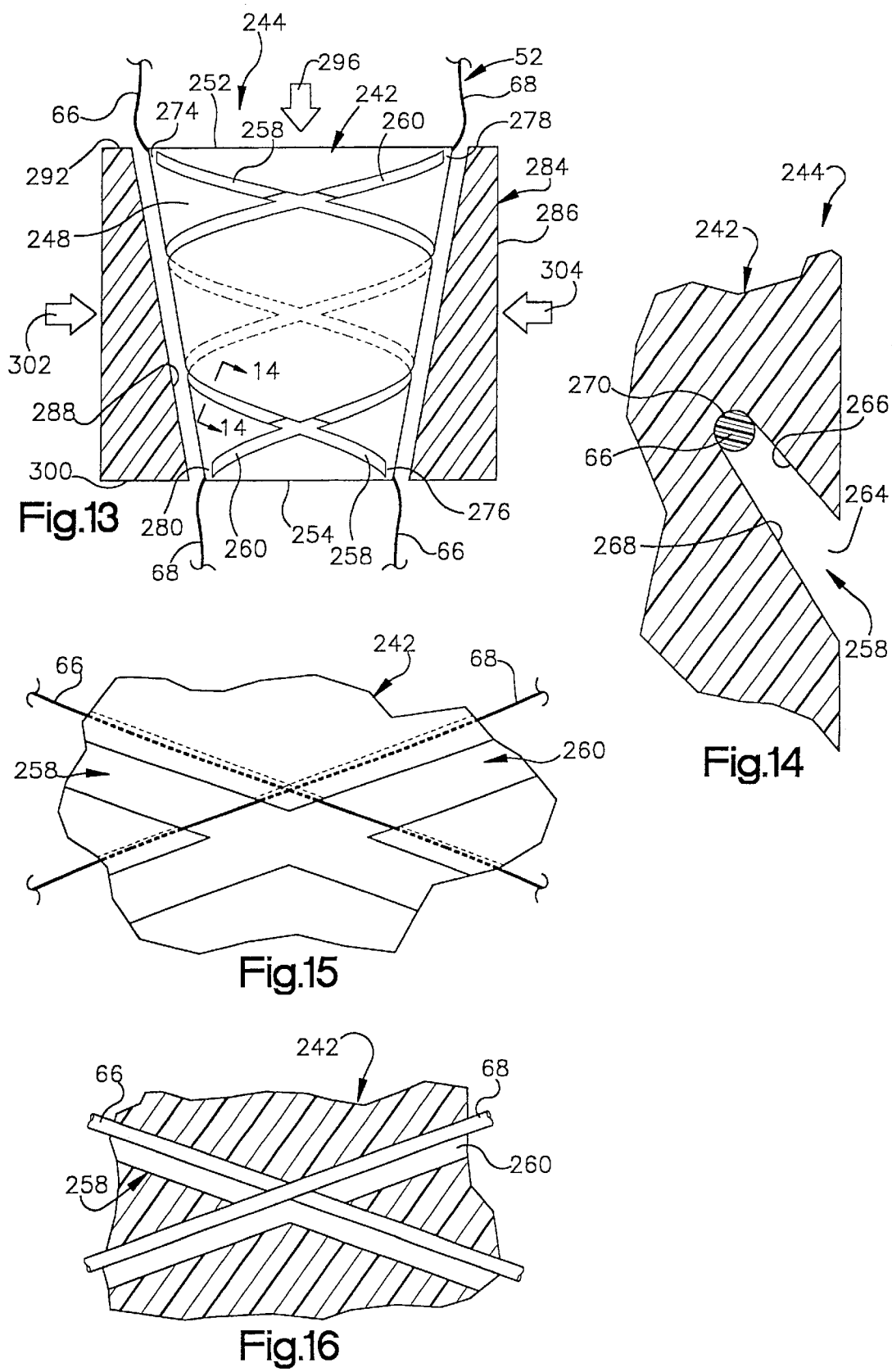

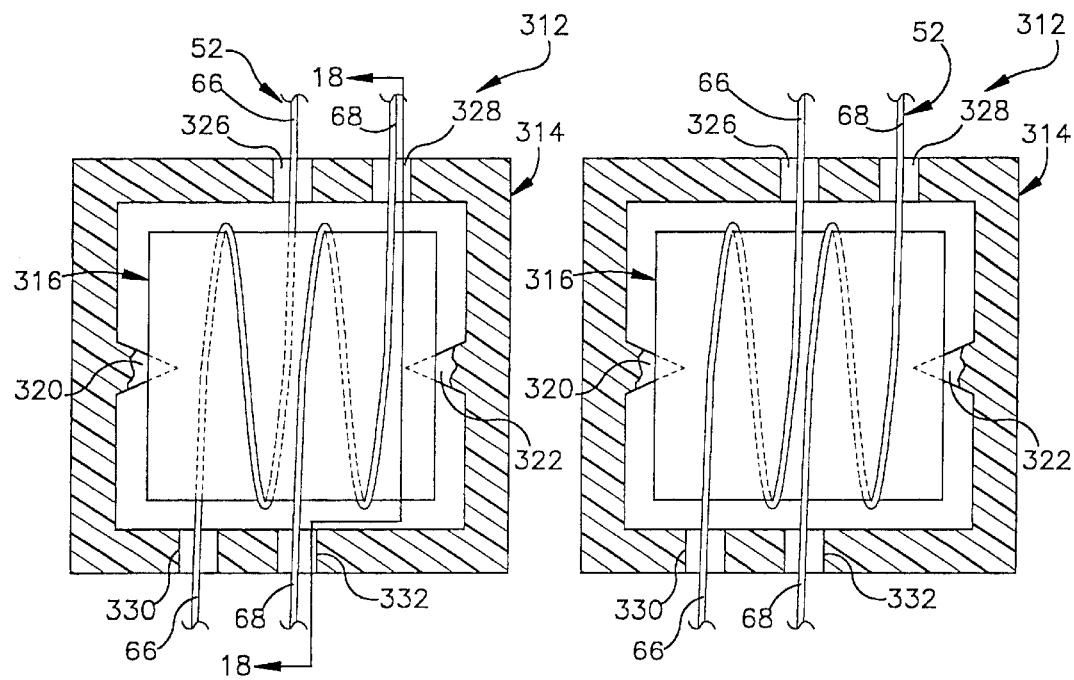
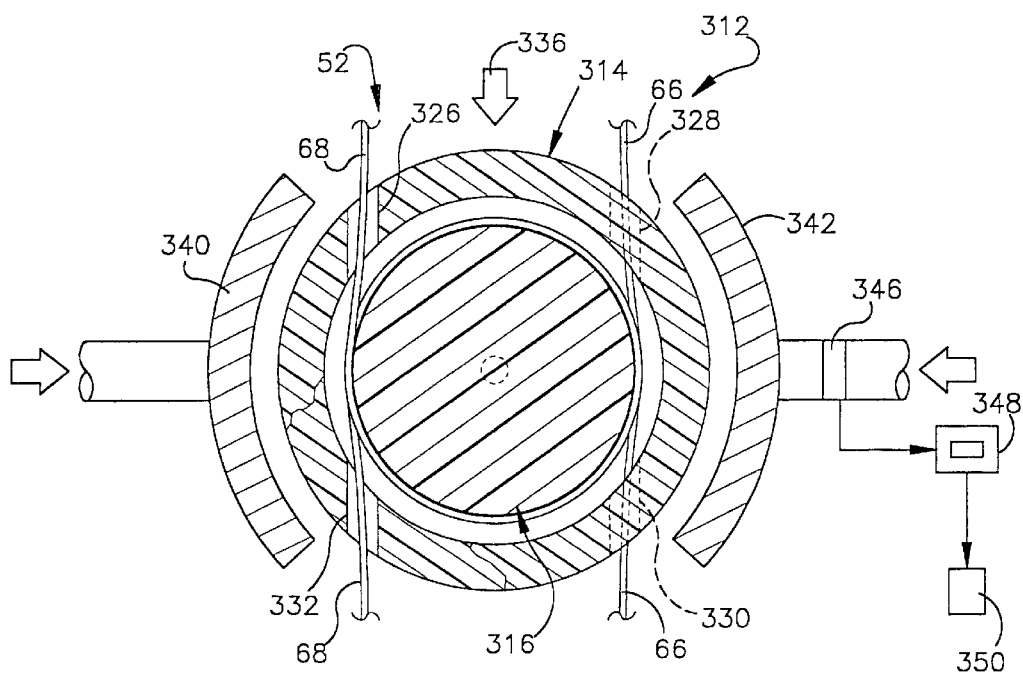

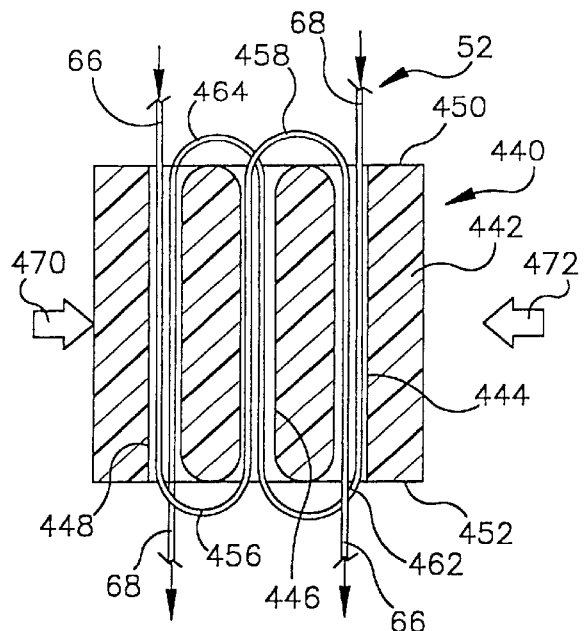

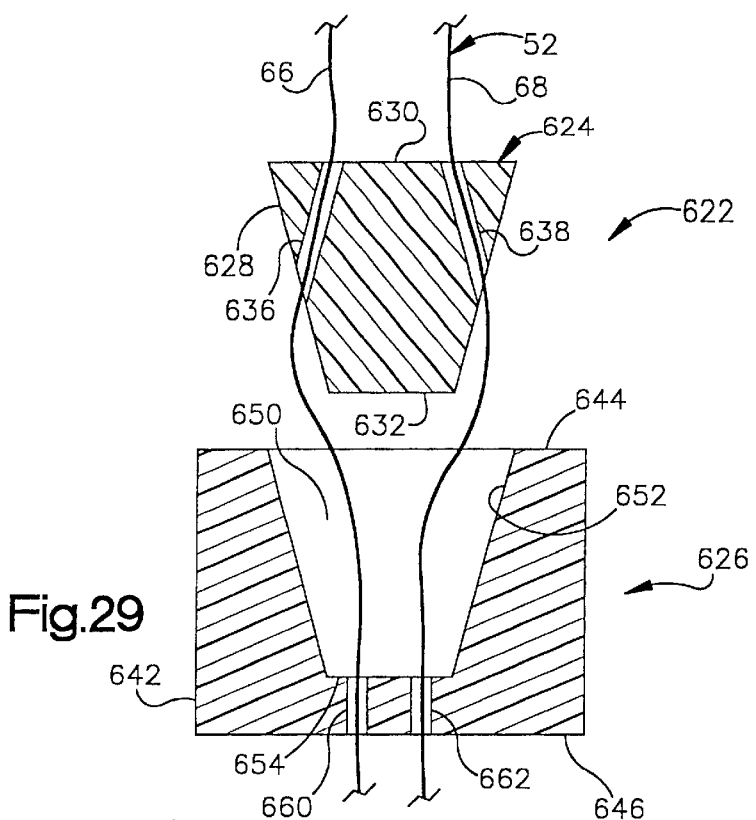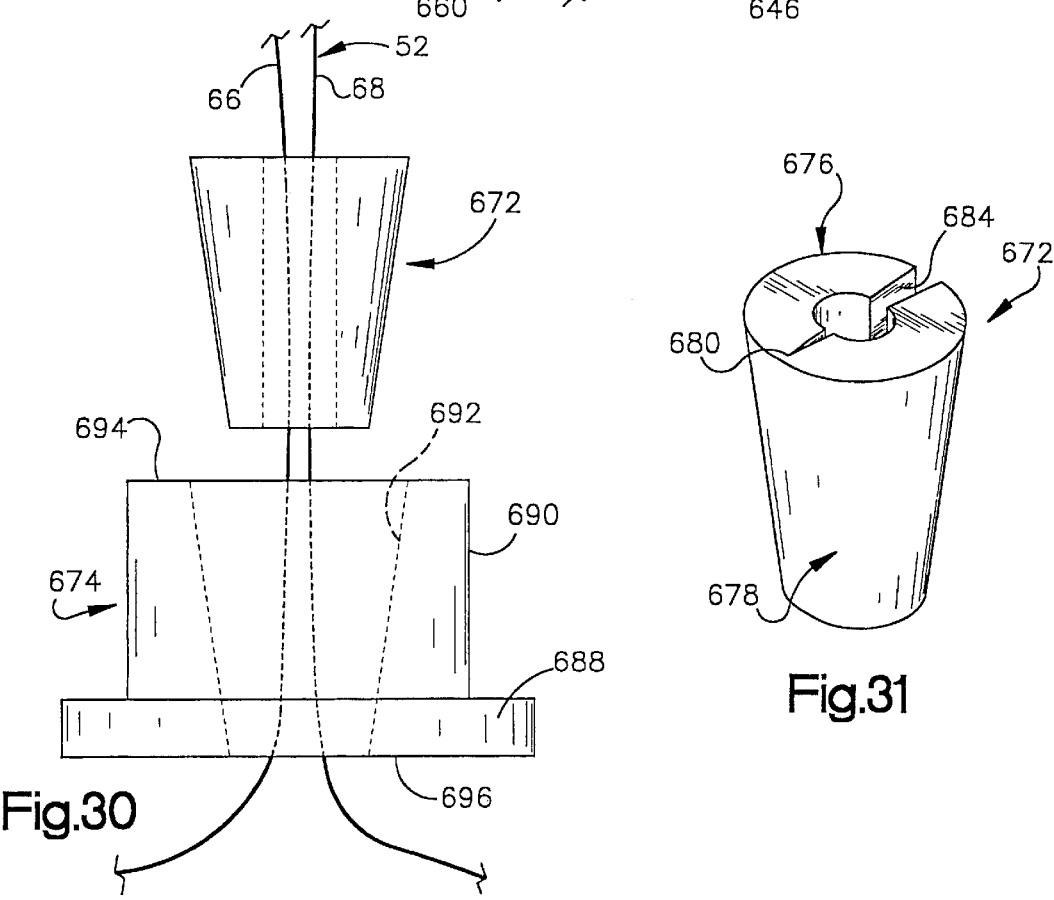

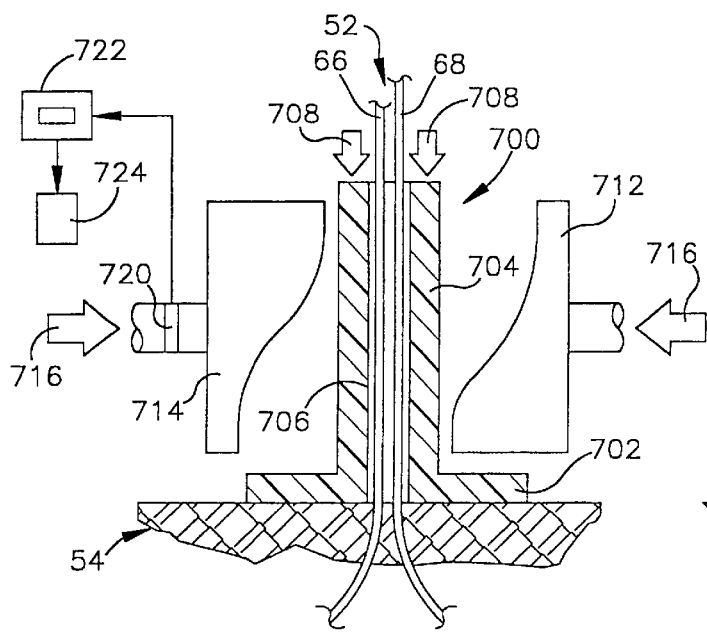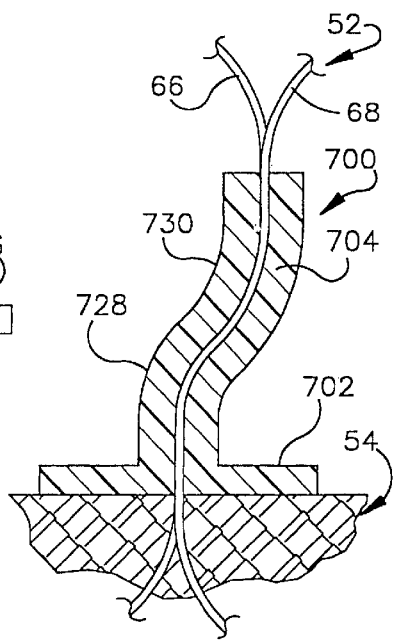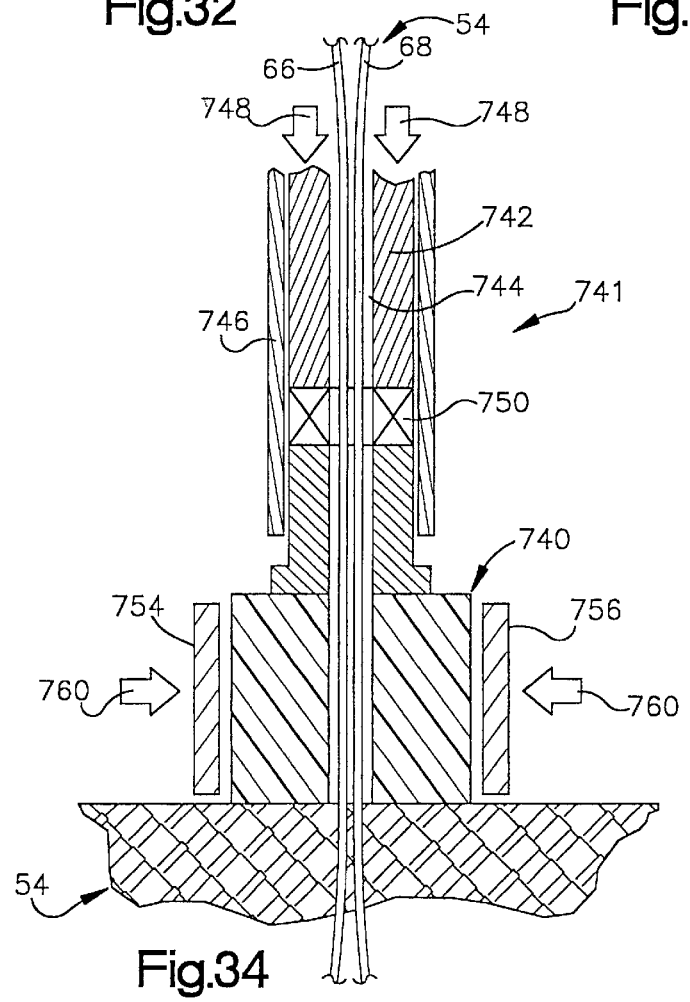
Fig.32
Fig.33
Fig.34

METHOD AND APPARATUS FOR SECURING A SUTURE

RELATED APPLICATIONS

This application is a divisional of application Ser. No. 09/429,100 filed Oct. 28, 1999 now U.S. Pat. No. 6,231,592. The aforementioned application Ser. No. 09/429,100 is itself a divisional of application Ser. No. 08/905,084 filed Aug. 1, 1997, now U.S. Pat. No. 6,010,525.

BACKGROUND OF THE INVENTION

The present invention relates to a new and improved method and apparatus for securing a suture against movement relative to body tissue by using a retainer to grip the suture.

Difficulty has been encountered in securing sutures against movement relative to body tissue. A knot may be tied in a suture to prevent loosening of the suture. However, the knot weakens a portion of the suture and reduces the overall force transmitting capability of the suture. In addition, a suture which is held by a knot applies force to a relatively small area of the body tissue and tends to cut or separate the body tissue. Many operations are conducted in very restricted space where the tying of a knot is difficult.

Various methods of securing a suture against movement relative to body tissue are disclosed in U.S. Pat. Nos. 3,513,848; 4,662,068; 4,935,028; 5,306,280; and 5,593,425. Although these and other known methods of securing a suture have, to a greater or lesser extent, been successful, it is desirable to simplify the securing of a suture against movement relative to body tissue. It is also desirable to be certain that the suture applies a desired amount of force to the body tissue when the suture is secured. The overall force transmitting capability of the suture should be maximized without concentrating the force at a small area on the body tissue.

SUMMARY OF THE INVENTION

The present invention provides a new and improved method and apparatus for use in securing a suture relative to body tissue. A suture retainer may be plastically deformed to grip the suture. The plastic deformation of the suture retainer may include pressing the material of the suture retainer against the suture by cold flowing material of the suture retainer. The plastic deformation of the material of the suture retainer may be performed while transmitting a predetermined force from the suture retainer to the body tissue.

The strength of a connection between the suture retainer and the suture may be increased by forming bends in the suture before deforming the material of the suture retainer. As the suture retainer is moved along the suture toward the body tissue, the bends are moved along the suture with the suture retainer. The bends may be formed by wrapping the suture around a circular portion of the suture retainer, by moving the suture through one or more passages in the suture retainer, by bending the suture around a member, and/or by deflecting a portion of the suture retainer through which the suture extends.

The suture retainer may be gripped with a tool which is moved along the suture to move the suture retainer toward the body tissue. The tool may be used to urge the suture retainer toward the body tissue with a predetermined minimum force. In addition, the tool may be used to plastically deform the material of the suture retainer when the suture retainer has been moved to a desired position.

BRIEF DESCRIPTION OF THE DRAWINGS

The foregoing and other features of the invention will become more apparent upon a consideration of the following description taken in connection with the accompanying drawings wherein:

FIG. 1 is a schematic illustration depicting the relationship of a suture retainer to a suture and body tissue prior to tightening of the suture;

FIG. 2 is an enlarged sectional view illustrating the manner in which the suture is wrapped around the suture retainer of FIG. 1 to form bends in the suture;

FIG. 3 is a schematic illustration depicting the manner in which the suture retainer of FIG. 2 is pressed against body tissue with a predetermined force and the manner in which a predetermined force is applied to an outer side surface of the suture retainer to plastically deform the suture retainer;

FIG. 4 is an enlarged fragmentary schematic illustration of a portion of FIG. 3 and depicting the manner in which the material of the suture retainer grips the suture;

FIG. 5 is an enlarged fragmentary view of a portion of FIG. 4 further illustrating the manner in which the material of the suture retainer grips the suture;

FIG. 13 is a schematic illustration depicting another embodiment of the suture retainer and the manner in which sections of a suture are wrapped in opposite directions to form bends in the suture;

FIG. 14 is a sectional view, taken generally along the line 14—14 of FIG. 13, illustrating the manner in which the suture is disposed in a groove in the suture retainer;

FIG. 15 is an enlarged fragmentary schematic illustration of a portion of FIG. 13, further illustrating the manner in which the suture is disposed in grooves formed in the suture retainer;

FIG. 16 is a fragmentary schematic sectional illustration of the manner in which the grooves and sections of the suture of FIG. 15 cross;

FIG. 17 is a schematic sectional view illustrating the manner in which a suture is wrapped around a roller in another embodiment of the suture retainer;

FIG. 18 is a schematic illustration depicting the manner in which the suture retainer of FIG. 17 is urged toward body tissue and the manner in which force is applied against the suture retainer to plastically deform the suture retainer;

FIG. 19 is a fragmentary schematic illustration, generally similar to FIG. 17, depicting an alternative manner of wrapping the suture around the roller;

FIG. 23 is a schematic sectional view depicting the manner in which the suture zig-zags through passages in another embodiment of the suture retainer;

FIG. 24 is a schematic sectional view illustrating the manner in which turns of a suture are wrapped in looped around another embodiment of the suture retainer;

FIG. 25 is a schematic sectional view illustrating the manner in which turns of a suture are wrapped in looped around another embodiment of the suture retainer;

FIG. 29 is a schematic sectional view of another two-section embodiment of the suture retainer prior to engagement of the two sections of the suture retainer;

FIG. 30 is a schematic illustration of another two-section embodiment of the suture retainer;

FIG. 31 is a pictorial illustration of an inner member used in the suture retainer of FIG. 30;

FIG. 32 is a schematic sectional illustration depicting the manner in which another embodiment of the suture retainer is pressed against a large area on body tissue with a predetermined force;

FIG. 33 is a schematic view of the suture retainer of FIG. 32 after the suture retainer has been plastically deformed to grip the suture;

FIG. 34 is a schematic illustration depicting the manner in which another embodiment of the suture retainer is pressed against body tissue and the manner in which force is applied against the suture retainer to effect plastic deformation of the suture retainer;

DESCRIPTION OF SPECIFIC PREFERRED EMBODIMENTS OF THE INVENTION

Embodiment of FIGS. 1–5

Figure 6:
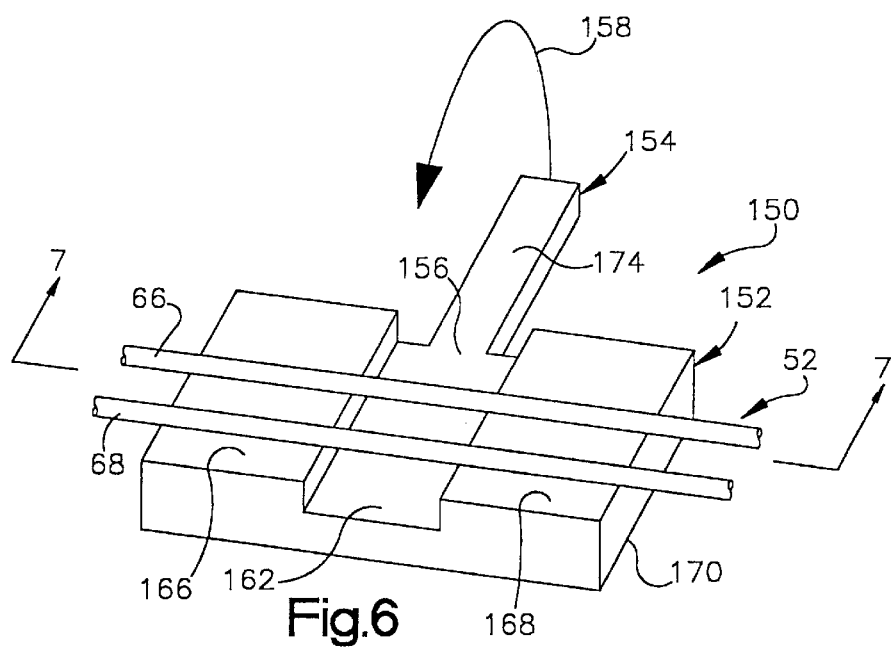
FIG. 6 is a schematic pictorial illustration depicting the manner in which a suture is positioned relative to a base of a second embodiment of the suture retainer.

A suture retainer 50 (FIG. 1) is utilized to secure a known suture 52 against movement relative to body tissue 54. The suture 52 extends through an outer layer 56 and an inner layer 58 of the body tissue. The suture 52 has been illustrated schematically in FIG. 1 as extending through passages 60 and 62 in the outer and inner layers 56 and 58 of body tissue 54. However, the suture 52 could be sewn through the body tissue without forming the passages 60 and 62 in the body tissue.

Although the suture 52 has been shown in FIG. 1 in association with soft body tissue, it is contemplated that the suture 52 could be associated with hard body tissue. It is also contemplated that the suture 52 could extend through a suture anchor in a manner similar to that disclosed in U.S. Pat. Nos. 5,584,862; 5,549,631; and/or 5,527,343.

The suture 52 has a left section 66 and a right section 68. The left and right sections 66 and 68 of the suture 62 extend through the suture retainer 50 (FIG. 2). If desired, the suture 52 could be integrally formed as one piece with the suture retainer 50. If this was done, an end of one of the sections 66 or 68 of the suture 52 would be connected with the suture retainer 50.

Although the sections 66 and 68 of the suture 52 could extend straight through the suture retainer 50, it is preferred to form a plurality of bends in the suture 52. In the illustrated embodiment of the invention, two bends 72 and 74 (FIG. 2) are formed in the left section 66 of the suture 52. Similarly, two bends 76 and 78 are formed in the right section 66 of the suture 52. If desired, a greater or lesser number of bends could be formed in each of the sections 66 and 68 of the suture 52.

The bends 72 and 74 (FIG. 2) are formed in the left section 66 of the suture 52 by wrapping a turn 82 in the left section of the suture around a portion of the suture retainer 50. Similarly, the bends 76 and 78 are formed in the right section 68 of the suture 52 by wrapping a turn 84 in the right section of the suture around a portion of the suture retainer 50. A single loop 86 is formed in the left section 66 of the suture 52 around a portion of the suture retainer. Similarly, a single loop 88 is formed in the right section 68 of the suture 52 around a portion of the suture retainer 50. A greater or lesser number of loops could be provided in the left and right sections 66 and 68 of the suture 52 if desired.

The suture retainer 50 has a spherical configuration. A cylindrical passage 92 extends through the center of the spherical suture retainer 50. If desired, the suture retainer 50 could have a different configuration. For example, the suture retainer 50 could have an oval or elliptical configuration. Although the passage 92 has a linear central axis, the passage could have a nonlinear central axis. If desired, a plurality of passages, having the same or different configurations, could be provided in the suture retainer 50.

The left and right sections 66 and 68 of the suture 52 extend through the passage 92. In addition, the left and right sections 66 and 68 of the suture 52 extend around a spherical outer side surface 94 of the suture retainer 50. Thus, the loop 86 in the left section 66 of the suture 52 extends around a left (as viewed in FIG. 2) hemispherical portion of the suture retainer 50. Similarly, the loop 88 extends around a right hemispherical portion of the suture retainer 50.

In the illustrated embodiment of the suture retainer 50, the left and right sections 66 and 68 of the suture 52 engage the smooth spherical outer side surface 94 of the suture retainer 50. However, it is contemplated that grooves could be provided in the outside of the suture retainer 50 to receive the turns 82 and 84 of the left and right sections 66 and 68 of the suture 52. Alternatively, projections could extend from the spherical outer side surface 94 of the suture retainer 50 to engage the suture 52.

After the suture 52 has been inserted through the suture retainer 50, in the manner illustrated schematically in FIG. 2, the suture retainer 50 is moved along the left and right sections 66 and 68 of the suture toward the body tissue 54 (FIG. 1). To move the suture retainer 50 along the left and right sections 66 and 68 of the suture 52, the left and right sections 66 and 68 of the suture are pulled upward (as viewed in FIGS. 1 and 2) to tension the sections of the suture. A downward (as viewed in FIG. 1) force is then applied against the suture retainer 50. This downward force causes the suture retainer 50 to slide in a downward direction along the suture 52 toward an upper side surface 98 of the body tissue 54 (FIG. 1).

As the suture retainer So slides downward along the left and right sections 66 and 68 of the suture 52, force is applied against the left section 66 of the suture 52 at the bend 74. This force causes loop 86 in the left section 66 of the suture 52 to move downward (as viewed in FIG. 2) along the left section of the suture. At the same time, force is applied against the right section 68 of the suture 52 at the bend 78. This force causes the loop 88 in the right section 68 of the suture 52 to move downward along the right section of the suture.

The suture retainer 50 is formed as one piece of a polymeric material having a relatively low coefficient of friction. Therefore, the two sections 66 and 68 of the suture 52 can readily slide along the outer side surface 94 and through the passage 92 in the suture retainer 50 as the suture retainer is moved downward toward the upper side surface 98 (FIG. 1) of the body tissue 54.

While a predetermined tension is maintained in the left and right sections 66 and 68 of the suture 52, the suture retainer 50 is pressed against the upper side surface 98 of the body tissue 54 (FIG. 3). This results in a connector section 102 (FIG. 1) of the suture 52 being pulled tightly against the inner layer 58 of body tissue. In order to obtain a desired tension in the left and right sections 66 and 68 and connector section 102 of the suture 52, the suture retainer 50 is pressed against the upper side surface 98 of the body tissue with a predetermined force, indicated schematically by an arrow 104 in the FIG. 3. The suture retainer 50 increases the surface area on the body tissue 54 against which force is applied.

Thus, while pulling on upper end portions of the left and right sections 66 and 68 of the suture 52 with a predetermined force, the suture retainer 50 is slid downward (as viewed in FIG. 1) along the left and right sections of the suture. The suture retainer 50 is pressed against the body tissue 54 with a predetermined force 104 (FIG. 3) which is sufficient to obtain a desired tension in the left and right sections 66 and 68 and connector section 102 of the suture 52. In this manner, a desired force, which has been preselected, is applied against the body tissue 54 by the suture 52 and suture retainer 50.

Although the suture retainer 50 applies force against a far greater surface area on the body tissue 54 than would be engaged by a know in the suture 52, a force distribution member or button may be placed between the suture retainer and the upper surface 98 of the body tissue. A second force distribution member or button may be placed between the connector section 102 of the suture and a lower side surface 108 (FIG. 1) of the body tissue 54. If this is done, the main area of engagement of the suture 52 with the body tissue 54 would be at the passages 60 and 62.

In accordance with a feature of the present invention, once the suture retainer 50 has been moved along the suture 52 and is being pressed against the body tissue 54 with a predetermined force 104 (FIG. 3), the suture retainer is plastically deformed to grip the left and right sections 66 and 68 of the suture. While the suture retainer 50 is being pressed against the body tissue 54 with the predetermined force 104 and the left and right sections 66 and 68 of the suture are being tensioned, a pair of force application members 112 and 114 are pressed against opposite sides of the suture retainer 50. The force applied against the suture retainer 50 by the force application members 112 and 114 plastically deforms the material of the suture retainer.

The plastic deformation of the suture retainer 50 is effective to cause cold flowing of material of the suture retainer. Force indicated by arrows 118 and 120 in FIG. 3, is applied against the suture retainer 50 by the force application members 112 and 114. This force is effective to cause flowing of the material of the suture retainer 50 at a temperature below a transition temperature range for the material of the suture retainer. Although the illustrated force application members 112 and 114 have flat force transmitting surfaces, each of the force application members could have force transmitting surfaces with a configuration corresponding to the configuration of a portion of a sphere.

The cold flowing of the material of the suture retainer 50 results in a collapsing of the passage 92 (FIG. 2) and in flowing of the material of the suture retainer 50 around the sections 66 and 68 of the suture 52. This enables the material of the suture retainer 50 to bond to and obtain a firm grip on the suture 52. The cold flowing of the material of the suture retainer 50 occurs at a temperature which is below the transition temperature of the material forming the suture retainer.

In the illustrated embodiment of the suture retainer 50, the material of the suture retainer flows around and grips the portion of the suture which was disposed in the passage 92. In addition, the force applied against the turns 82 and 84 by the force application members 112 and 114 is sufficient to embed the turns 82 and 84 of the suture 52 in the material of the suture retainer 50 to further grip the suture. If the turns 82 and 84 are disposed in grooves in the outside of the suture retainer, the material of the suture retainer would more firmly grip the portion of the suture 52 forming the turns 82 and 84. If desired, grooves could be formed in the cylindrical side surface of the passage 92 to receive the sections 66 and 68 of the suture 52.

A transducer or load cell 114 (FIG. 3) is connected with the force application member 112 to measure the amount of force, indicated by the arrows 118 and 120, which is applied against the suture retainer 50. A display unit 126 is connected with the load cell 124 and provides an output indicative of the force being applied against opposite sides of the suture retainer 50 by the force application members 112 and 114. After a predetermined minimum force has been applied against the suture retainer 50 for a predetermined minimum time by the force application members 112 and 114, an output from the display unit 126 activates an indicator 130 to indicate to a surgeon that the desired plastic deformation of the suture retainer 50 has occurred. The force application members 112 and 114 can then be withdrawn from the suture retainer 50.

During the time in which the force application members 112 and 114 are applying the clamping forces 118 and 120 against opposite sides of the suture retainer 50, the suture retainer is pressed against the upper side surface 98 of the body tissue 54 with a predetermined force, indicated at 104 in FIG. 3. In addition, a predetermined tension is maintained in sections 66 and 68 of the suture 52 extending upward from the suture retainer 50. Upon disengagement of the force application members 112 and 114 from the suture retainer 50, the application of the downward (as viewed in FIG. 3) force 104 against the suture retainer 50 is interrupted. The upward tensioning of the sections 66 and 68 of the suture 52 is also interrupted.

The application of the clamping forces 118 and 120 against opposite sides of the suture retainer 50 causes cold flowing of the material of the suture retainer. As this occurs, the material of the suture retainer 50 moves between and extends around the portions of the left and right sections 66 and 68 of the suture 52 disposed in the passage 92 (FIG. 2). Thus, a portion 134 (FIGS. 2 and 4) and a portion 136 of the left section 66 of the suture 52 are fully enclosed by the material of the suture retainer 50. A cold bonding of the material of the suture retainer 50 with the exterior surfaces of the portions 134 136 of the left section 66 of the suture retainer securely interconnects the material of the suture retainer and the suture 52.

Similarly, the portions 138 and 140 of the right section 68 of the suture 52 disposed in the passage 92 (FIG. 2) are surrounded by and bonded with the material of the suture retainer 50 (FIG. 4). The manner in which the material of the suture retainer 50 extends completely around and is connected with the length or portion 138 of the right section 68 of the suture 52 is illustrated schematically in FIG. 5. It should be understood that the permanent deformation of the material of the suture retainer 50 occurs as a result of compression of the material of the suture retainer while the material is at a temperature close to the temperature of the body tissue 54. This temperature is below the transition temperature for the material of the suture retainer 50.

Once the suture retainer 50 has been plastically deformed to securely grip the suture 52, the suture may be knotted if desired. Thus, a knot may be formed between the portions of the sections 66 and 68 of the suture 52 which extend upward (as viewed in FIGS. 1-3) from the retainer 50. Such a knot would provide additional protection against the suture working loose under the influence of varying loads over an extended period of time. Since the suture retainer 50 is disposed between the knot and the body tissue 54, the knot will not reduce the overall force transmitting capability of the suture 52. However, it is believed that forming a knot in the sections 66 and 68 of the suture 52 adjacent to the upper end of the suture retainer 50 will not be necessary.

The suture retainer 50 may be formed of many different materials. However, it is believed that it will be preferred to form the suture retainer 50 of a biodegradable polymer. One biodegradable polymer which may be utilized is polycaperlactone. Alternatively, the suture retainer 50 could be formed of polyethylene oxide terephthalate or polybutylene terephthalate. It is also contemplated that other biodegradable or bioerodible copolymers could be utilized if desired.

Although it is preferred to form the suture retainer 50 of a biodegradable material, the suture retainer could be formed of a material which is not biodegradable. For example, the suture retainer could be formed of an acetyl resin, such as "Delrin" (trademark). Alternatively, the suture retainer 50 could be formed of a para-dimethylamino-benzenediazo sodium sulfonate, such as "Dexon" (trademark).

It is preferred to effect the cold flowing of the material of the suture retainer 50 without the addition of heat. However, it is contemplated that the suture retainer 50 could be heated to a temperature which is somewhat above the temperature of the body tissue 54. If desired, heat could be transmitted to the suture retainer 50 through the force application members 112 and 114 (FIG. 3). Although the suture retainer 50 may be heated, the suture retainer would be maintained at a temperature below the transition temperature for the material of the suture retainer.

In the illustrated embodiment of the invention, the suture 52 is separate from the suture retainer 50. However, one of the sections 66 or 68 of the suture 52 could be fixedly connected with the suture retainer 50. This could be accomplished with a suitable fastener or by forming the suture 52 integrally as one piece with the suture retainer. This would result in the suture retainer 50 sliding along only one of the sections 66 or 68 of the suture 52.

The suture 52 may be formed of material or synthetic materials. The suture 52 may be a monofilament or may be formed of a plurality of interconnected filaments. The suture 52 may be biodegradable or nonbiodegradable. It may be preferred to form the suture 52 of the same material as the suture retainer 50. However, the suture 52 could be formed of a material which is different than the material of the suture retainer.

The use of the suture retainer 50 eliminates the necessity of forming a knot in the suture 52. By eliminating the formation of a knot in the suture 52, the overall force transmitting capability of the suture is increased. In addition to increasing the overall force transmitting capability of the suture 52, the suture retainer 50 increases the surface area on the body tissue 54 (FIG. 1) against which force is applied by the suture. This tends to minimize any tendency for the suture 52 to cut or separate the body tissue.

It is believed that it may be preferred to position the left and right sections 66 and 68 of the suture 52 relative to the body tissue 54 (FIG. 1) before winding the two sections of the suture around the suture retainer 50. However, one of the sections 66 or 68 of the suture 52 may be wound around the suture retainer 50 before the suture is positioned in the passages 60 and 62 in the body tissue 54. For example, the left section 66 of the suture 52 may e wound around the suture retainer 52 to form the bends 72 and 74 and the loop 86 (FIG. 2) while the suture is spaced from the body tissue 54. The right section 68 of the suture is then inserted through the passages 60 and 62 (FIG. 1) in the body tissue 54. The right section 68 of the suture 52 is then wound around the suture retainer 50 to form the bends 76 and 78 and loop 88 (FIG. 2).

Figure 7:
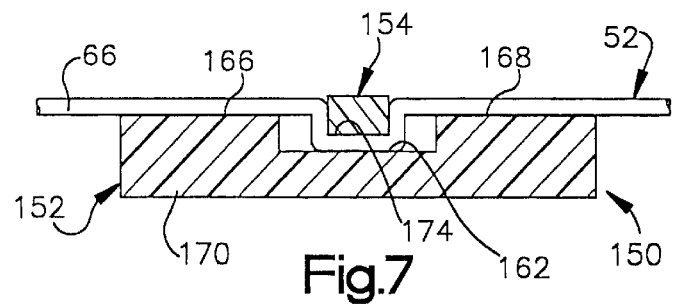
FIG. 7 is a schematic illustration, taken along the line 7—7 of FIG. 6, depicting the manner in which a movable arm presses a portion of the suture into a groove formed in the base of the suture retainer to form bends in the suture.
Figure 8:
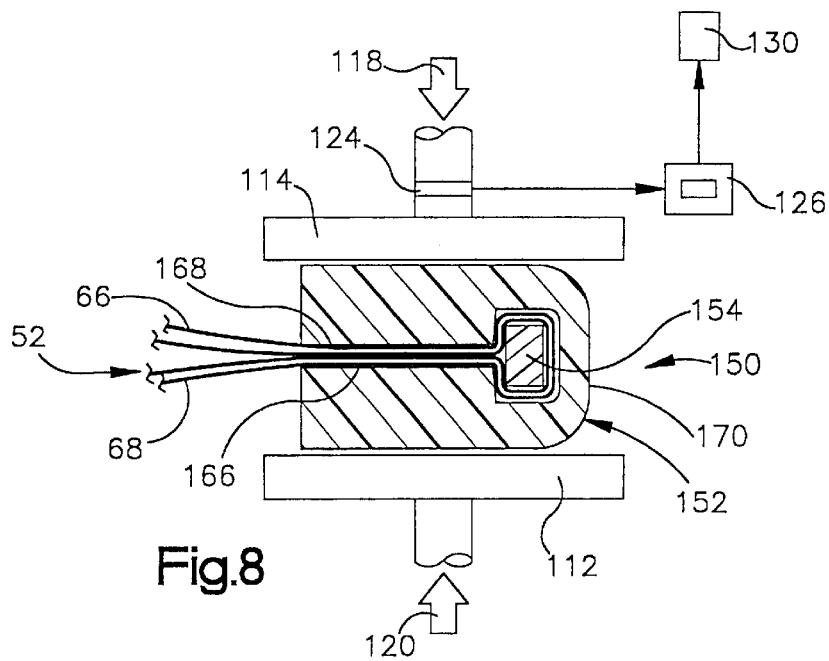
FIG. 8 is a schematic illustration depicting the manner in which force is applied against the suture retainer of FIGS. 6 and 7 to plastically deform the suture retainer.

Embodiment of FIGS. 6–8

In the embodiment of the invention illustrated in FIGS. 1–5, complete loops 86 and 88 are formed in the sections 66 and 68 of the suture 52. In the embodiment of the invention illustrated in FIGS. 6–8, partial loops are formed in each of the sections of the suture. Since the embodiment of the invention illustrated in FIGS. 6–8 is similar to the embodiment of the invention illustrated in FIGS. 1–5, similar terminology will be utilized to identify similar components. It should be understood that one or more features of the embodiment of the invention illustrated in FIGS. 1–5 may be used with the embodiment of the invention illustrated in FIGS. 6–8.

A suture retainer 150 is utilized to secure a suture 52 against movement relative to body tissue. The suture 52 has sections 66 and 68 which engage body tissue in the same manner as previously described in conjunction with the embodiment of the invention illustrated in FIGS. 1-5. Although the suture 52 is illustrated in FIG. 1 in association with soft body tissue, it is contemplated that the suture 52 could be utilized in association with hard body tissue and/or one or more suture anchors.

The suture retainer 150 includes a rectangular base or body section 152 and a movable post or locking section 154. The post or locking section 154 is integrally formed as one piece with the base 152. The post or locking section is hingedly connected with the base 152 at a connection 156. The post 154 is pivotal relative to the base at the connection 156 in the manner indicated schematically by the arrow 158 in FIG. 6.

The base 152 has a central groove 162 which is aligned with the post 154. The groove 162 has a rectangular cross sectional configuration. The groove 162 has a cross sectional area which is greater than the cross sectional area of the post 154. In the illustrated embodiment of the suture retainer 150, the post 154 and groove 162 both have a rectangular cross sectional configuration. However, the post and groove could have a different cross sectional configuration if desired. For example, the post 154 and groove 162 could have a semi-circular cross sectional configuration.

The base 152 has a pair of flat rectangular upper (as viewed in FIGS. 6 and 7) side surfaces 166 and 168. The flat side surfaces 166 and 168 extend in opposite directions from the groove 162 and extend parallel to a flat rectangular bottom surface 170. The suture retainer 150 is formed from a single piece of a biodegradable polymer, such as polycaperlactone. Of course, other biodegradable or bioerodible copolymers could be utilized to form the suture retainer 150. It is contemplated that the suture retainer 150 may be formed of materials which are not biodegradable.

When the suture retainer 150 is to be utilized to hold the sections 66 and 68 of the suture 52 against movement relative to body tissue, the post 154 is pivoted from its initial or extended position, shown in FIG. 6, to its engaged or locking position, shown in FIG. 7. As the post 154 is pivoted to the engaged position of FIG. 7, a flat side surface 174 of the post is pressed against the sections 66 and 68 of the suture to force the sections into the groove 162. The post is effective to clamp or hold the sections 66 and 68 of the suture 52 against movement relative to the base 152 upon movement of the post to the engaged position shown in FIG. 7.

Once the post 154 has been moved to the engaged position shown in FIG. 7, the base 152 is bent from the flat orientation of FIGS. 6 and 7 to the folded orientation of FIG. 8. Once the base 152 has been folded, a pair of force application members 112 and 114 engage opposite sides of the bottom or outer surface 170 of the base. The force application members 112 and 114 are then pressed toward each other, in the manner indicated schematically by the arrows 118 and 120 in FIG. 8, to apply pressure against the suture retainer 150.

At this time, the suture retainer 150 is at a temperature below the transition temperature of the material forming the suture retainer. Thus, the suture retainer 150 is at a temperature which is approximately the same as the temperature of the body tissue relative to which the suture retainer 150 is being utilized to secure the suture 52. The force applied against the suture retainer 150 by the force application members 112 and 114 plastically deforms the material of the suture retainer. This results in a cold flowing of the material of the suture retainer 150 under the influence of the force applied against the suture retainer by the force application members 112 and 114.

A transducer or load cell 124 measures the force 118 and 120 applied against the base 152 of the suture retainer 150.

The load cell 124 provides an output signal to a display unit 126. The output signal provided by the transducer 124 corresponds to the magnitude of the force applied against opposite sides of the suture retainer 150 by the members 112 and 114.

After a predetermined minimum force has been applied against opposite sides of the suture retainer 150 for a sufficient period of time to effect a cold flowing of the material of the suture retainer, an output signal from the display unit 126 activates an indicator 130. The output from the indicator 130 indicates to a surgeon and/or other medical personnel that the force has been applied against opposite sides of the suture retainer 150 by the force application members 112 and 114 for a period of time sufficient to cause cold flowing of the material of the suture retainer. The cold flowing of the material of the suture retainer 150 results in a secure interconnection between the material of the suture retainer 150 and the sections 66 and 68 of the suture 52.

In the embodiment of the invention illustrated in FIGS. 6–8, the suture 52 is separate from the suture retainer 150. However, the suture 52 could be fixedly connected to or integrally formed as one piece with the suture retainer 150. For example, the base 152 could be integrally formed with the section 66 of the suture 52 if desired.

Embodiment of FIGS. 9–12

In the embodiment of the invention illustrated in FIGS. 1–5, the sections 66 and 68 of the suture 52 extend through a passage formed in a spherical suture retainer 50. In the embodiment of the invention illustrated in FIGS. 9–12, the sections of the suture extend along a groove formed in the outside of a suture retainer. Since the embodiment of the invention illustrated in FIGS. 9–12 is similar to the embodiment of the invention illustrated in FIGS. 1–5, similar terminology will be utilized to identify similar components. It should be understood that one or more features of the embodiments of the invention illustrated in FIGS. 1–8 may be used with the embodiment of the invention illustrated in FIGS. 9–12.

A suture retainer 180 (FIG. 9) is utilized to secure a suture 52 against movement relative to body tissue 54. Although the body tissue 54 is soft body tissue, it is contemplated that the suture retainer 180 could be utilized to secure the suture 52 against movement relative to hard body tissue, such as bone. The suture retainer 180 may be used either with or without a suture anchor.

The suture retainer 180 has a cylindrical main section or body 184. The body 184 has a cylindrical outer side surface 186. Flat circular end surfaces 188 and 190 extend perpendicular to a longitudinal central axis of the cylindrical side surface 186. In the illustrated embodiment of the suture retainer 180, the body 184 is cylindrical and has a linear longitudinal central axis. If desired, the body 184 could be rectangular and/or have a nonlinear longitudinal central axis.

A helical groove 194 is formed in the body 184. The helical groove 194 has a constant pitch. Therefore; turns of the groove 194 are equally spaced. However, if desired, the pitch of the turns of the groove 194 could vary along the length of the body 184.

The helical groove 194 has a central axis which is coincident with the central axis of the body 184 and cylindrical outer side surface 186 of the suture retainer 180. A radially inner portion of the helical groove 194 defines a right circular cylinder which is coaxial with the outer side surface 186 of the body 184. However, the radially inner portion of the helical groove 194 could define a right circular cone or other configuration if desired.

The left and right sections 66 and 68 of the suture 52 extend through the groove 194 and around body tissue 54. It is believed that it will be advantageous to provide the helical groove 194 with retainers or bridge sections 198 and 200 which extend across the open ends of the helical groove. The bridge sections 198 and 200 are integrally formed as one piece with the body 184. The bridge sections 198 and 200 prevent the sections 66 and 68 of the suture 52 from pulling out of the helical groove 194 during positioning of the suture retainer 180 in a human patient's body. However, the bridge sections 198 and 200 may be omitted if desired.

Figure 9:
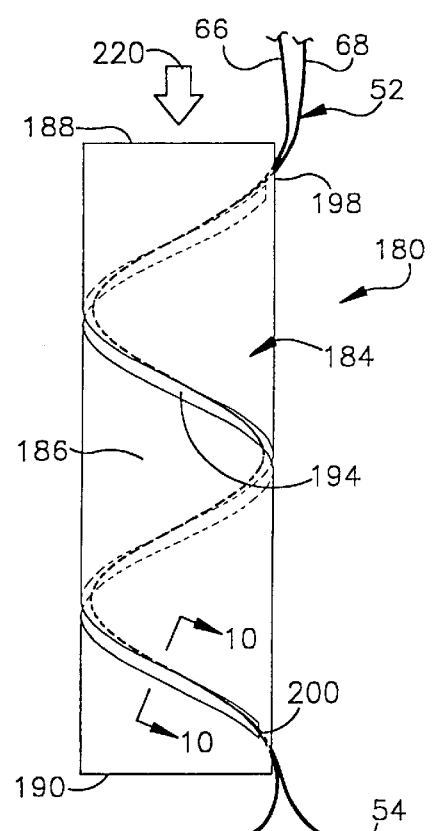
FIG. 9 is a schematic illustration depicting the manner in which a suture is wrapped around another embodiment of the suture retainer to form bends in the suture.
Figure 10:
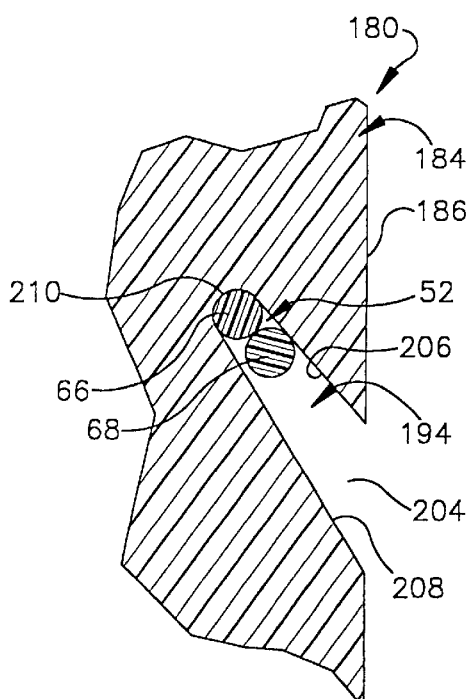
FIG. 10 is an enlarged fragmentary sectional view, taken generally along the line 10—10 of FIG. 9, illustrating the manner in which the suture is disposed in a groove in the suture retainer.
Figure 11:
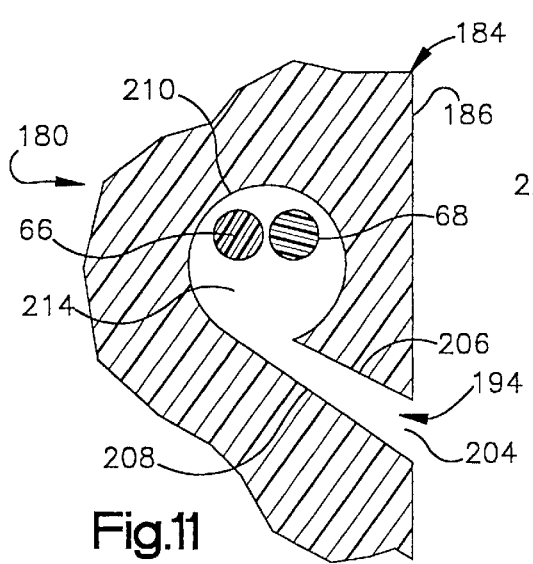
FIG. 11 is a fragmentary sectional view, generally similar to FIG. 10, illustrating an alternative configuration for the groove in the suture retainer of FIG. 9.

The helical groove 194 has a generally U-shaped cross sectional configuration (FIG. 10). Thus, the helical groove 194 has an open mouth or entrance 204. A pair of. side surfaces 206 and 208 slope radially inward and axially upward (as viewed in FIGS. 9 and 10) from the entrance 204. An arcuate bottom surface 210 of the groove 194 extends between the side surfaces 206 and 208.

The section 66 of the suture 52 is disposed in engagement with the bottom surface 210 of the helical groove 194. The section 68 of the suture 52 is disposed in engagement with the section 66 of the suture (FIG. 10). If desired, the size of the arcuate bottom surface 210 of the groove 194 could be increased to enable both sections 66 and 68 of the suture 52 to engage the bottom surface. The groove 194 may be provided with a configuration similar to the configuration shown in FIG. 11. Thus, in FIG. 11, the side surfaces 206 and 208 of the helical groove 194 extend inward from the open entrance 204 to an arcuate bottom surface 210 which forms a major portion of a circle. The bottom surface 210 of FIG. 11 defines a recess 214 in which the two sections 66 and 68 of the suture are disposed. It is believed that the bridge sections 198 and 200 will probably be omitted with the embodiment of the groove 194 illustrated in FIG. 11.

The cylindrical body 184 of the suture retainer 180 is molded from a single piece of a biodegradable polymer. For example, the body 184 of the suture retainer 180 may be molded from polycaperlactone. Alternatively, the body 184 of the suture retainer 180 could be molded of polyethylene oxide terephthalate or polybutylene terephthalate. Of course, the body 184 of the suture retainer 180 could be molded as one piece of other biodegradable or bioerodible copolymers if desired. Although it is preferred to form the body 184 of biodegradable materials, the body could be formed of materials which are not biodegradable. For example, the body 184 could be formed of "Delrin" (trademark).

The left and right sections 66 and 68 (FIG. 9) of the suture 52 are inserted into the helical groove 194 in the body 184 of the suture retainer 180. At this time, the body 184 of the suture retainer 180 is spaced from the body tissue 54. It is believed that insertion of the left and right sections 66 and 68 of the suture 52 into the helical groove 194 will be facilitated if the bridge sections 198 and 200 are omitted. However, if the bridge sections 198 and 200 are omitted, difficulty may be encountered in maintaining the sections 66 and 68 of the suture 52 in the helical groove 194.

As the left and right sections 66 and 68 of the suture 52 are inserted into the helical groove 194 (FIG. 9), the sections of the suture are wrapped around the body 184 of the suture retainer 180. As this occurs, a plurality of helical loops are formed in the left and right sections 66 and 68 of the suture 52. Once the suture 52 has been inserted into the helical groove 194, a plurality of circular turns are maintained in the left and right sections 66 and 68 of the suture 52 by the helical groove 194. Therefore, a continuous series of smooth arcuate bends, which are free of stress inducing discontinuities, is maintained in the suture 52 by the helical groove 194.

After the suture 52 has been inserted into the helical groove 194, the suture retainer 180 is moved along the suture toward the body tissue 54 (FIG. 9). During this movement of the suture retainer 180 along the suture 52, the left and right sections 66 and 68 of the suture are tensioned. The radially inward and axially upward sloping configuration of the helical groove 194 (FIGS. 10 and 11) results in the left and right sections 66 and 68 of the suture being pulled toward the arcuate bottom surface 210 of the groove. This results in the body 184 of the suture retainer 180 maintaining the helical loops in the left and right sections 66 and 68 of the suture 52 as the suture retainer 180 moves toward the body tissue 54.

As the suture retainer 180 moves toward the body tissue 54 (FIG. 9), the left and/or right sections 66 and 68 of the suture 52 slide along the arcuate bottom surface 210 (FIG. 10) of the groove 194. The groove 194 imparts a helical configuration to the portion of the suture 52 disposed in the groove. As the body 184 of the suture retainer 180 moves downward toward the body tissue 54, the portion of the suture 52 having a helical configuration moves downward toward the body tissue.

As the suture retainer 180 is slid along the tensioned sections 66 and 68 of the suture 52, the tensioning force in the suture pulls the suture toward the bottom surface 210 of the helical groove 194. The biodegradable copolymer forming the body 184 of the suture retainer 180 has a low coefficient of friction. This minimizes the force 220 required to move the suture retainer along the left and right sections 66 and 68 of the suture 52 toward the body tissue 54.

The suture retainer 180 is moved along the taut left and right sections 66 and 68 of the suture 52 until the leading end surface 190 of the body 184 of the suture retainer 180 engages the body tissue 54 (FIG. 9). The force 220 is then increased to a predetermined magnitude while maintaining a predetermined tension in the left and right sections 66 and 68 of the suture 52. This results in the suture 52 being pulled tightly around the body tissue and exerting a predetermined force against the body tissue.

It is contemplated that the magnitude of the force 220 (FIG. 9) with which the suture retainer 190 is pressed against the body tissue 54 will be measured to be certain that the force has a desired magnitude. The force 220 may be measured with a suitable transducer, such as a load cell or a force measuring device having a spring which is compressed to a predetermined extent by the application of the desired force against the body tissue 54. Rather than engaging the body tissue 54 directly with the leading end surface 190 of the suture retainer 180, a suitable force transmitting member, such a button, could be provided between the suture retainer and the body tissue.

While the suture retainer 180 is being pressed against the body tissue 54 with the predetermined force 220 and the sections 66 and 68 of the suture 52 are being tensioned with a predetermined force, the left and right sections 66 and 68 of the suture 52 are gripped by plastically deforming the material of the suture retainer. To plastically deform the material of the suture retainer, a plurality of force application members 224, 226 and 228 (FIG. 12) are pressed against the cylindrical outer side surface 186 of the suture retainer 180. Since the outer side surface 186 of the suture retainer 180 has a cylindrical configuration, the force application members 224, 226 and 228 have an arcuate configuration and are formed as portions of a circle. However, the force application members 224, 226 and 228 could have the flat configuration of the force application members 112 and 114 of FIG. 3.

Figure 12:
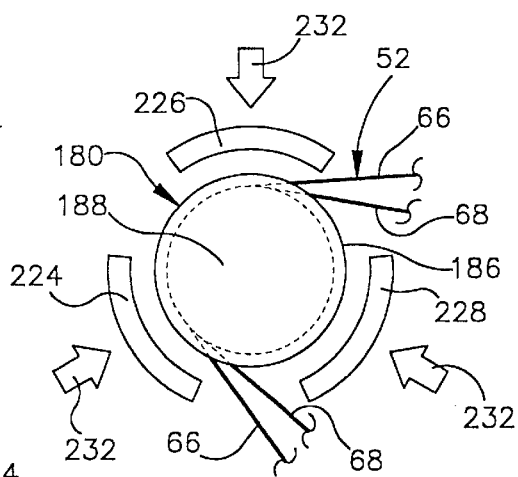
FIG. 12 is a schematic illustration depicting the manner in which force is applied against the suture retainer of FIG. 9 to plastically deform the suture retainer and grip the suture.

The force application members 224, 226 and 228 are pressed against the outer side surface 186 of the suture retainer 180 with a predetermined force, indicated by the arrows 232 in FIG. 12. This force has a magnitude and is applied for a length of time sufficient to cause cold flowing of the material of the body 184 of the suture retainer 180. The plastic deformation of the material of the body 194 of the suture retainer 180 results in the helical groove 194 being collapsed and the material of the suture retainer being pressed against the left and right sections 66 and 68 of the suture 52. The resulting cold bonding of the material of the suture retainer 180 with the left and right sections 66 and 68 of the suture 52 secures in the suture retainer against movement relative to the suture.

The cold flowing of the material of the body 184 of the suture retainer 180 occurs with the body of the suture retainer at substantially the same temperature as the temperature of the body tissue 54 (FIG. 9). Thus, the cold flowing of the material of the body 184 of the suture retainer 180 occurs at a temperature below the transition temperature of the material forming the body 184 of the suture retainer 180. However, if desired, some heat may be added to the body 184 to facilitate plastic deformation of the body of the suture retainer 180.

The suture retainer 180 eliminates the necessity of forming a knot in the suture 52. The formation of a knot in the suture 52 would cause a stress concentration in the suture and would decrease the overall force transmitting capability of the suture. By eliminating the knot, the overall force transmitting capability of the suture 52 is increased. However, if desired, a knot could be formed in the sections 66 and 68 of the suture 52 at a location above (as viewed in FIG. 1) the suture retainer 180. Since the suture retainer 180 would be disposed between this knot and the body tissue 54, the knot would not decrease the overall force transmitting capability of the suture 52.

In the embodiment of the invention illustrated in FIGS. 9–12, a single helical groove 194 is formed in the body 184 of the suture retainer 180. It is contemplated that a pair of spaced apart helical grooves could be formed in the body 184 of the suture retainer 180. If this was done, the two helical grooves would be wrapped in the same direction around the body 184 of the suture retainer 180 and would be offset from each other by 180N about the circumference of the cylindrical body of the suture retainer. The left section 66 of the suture 52 would be disposed in one of the helical grooves and the right section 68 of the suture would be disposed in the other helical groove.

By having a pair of spaced apart helical grooves in the body 184 of the suture retainer 180, in the manner set forth in the preceding paragraph, the left and right sections 66 and 68 of the suture 52 would exit from the lower (as viewed in FIG. 9 end of the suture retainer at diametrically opposite locations on the circular end surface 190. This embodiment of the suture retainer 180 would have the advantage of having a relatively large area of engagement with the body tissue 54. Thus, the tension in the suture would press the flat circular end surface 190 on the suture retainer against the body tissue.

In the illustrated embodiment of the invention, the suture 52 is separate from the suture retainer 180. However, if desired, the suture 52 could be fixedly connected with or integrally formed as one piece with the suture retainer. For example, the left section 66 of the suture 52 could be fixedly connected with the body 184 of the suture retainer 180 by a suitable fastener. If this was done, only the right section 68 of the suture 52 would be received in the groove 194.

Embodiment of FIGS. 13–16

In the embodiment of the invention illustrated in FIGS. 9–12, the left and right sections 66 and 68 of the suture 52 are wrapped in the same direction around the cylindrical body 184 of the suture retainer 180. In the embodiment of the invention illustrated in FIGS. 13–16, the sections of the suture are wrapped in opposite directions around a conical body of a suture retainer. Since the embodiment of the invention illustrated in FIGS. 13–16 is similar to the embodiment of the invention illustrated in FIGS. 9–12, similar terminology will be utilized to identify similar components. It should be understood that one or more features of the embodiments of the invention illustrated in FIGS. 1–12 may be used with the embodiments of the invention illustrated in FIGS. 13–16.

A suture 52 (FIG. 13) has left and right sections 66 and 68 which are wrapped in opposite directions around a conical body 242 of a suture retainer 244. Thus, as viewed from above, the left section 66 of the suture 52 is wrapped in a counterclockwise direction around the body 242 of the suture retainer 244. The right section 68 of the suture 52 is wrapped in a clockwise direction around the body 242 of the suture retainer 244.

The left and right sections 66 and 68 of the suture 52 are wrapped for approximately 1½ turns around the body 242 of the suture retainer 244. Therefore, the left section 66 of the suture 52 moves from the left side of the upper end (as viewed in FIG. 13) of the body 242 of the suture retainer 244 to the right side of the lower end of the body of the suture retainer. Similarly, the right section 68 of the suture 52 moves from the upper right side of the body 242 of the suture retainer 244 to the lower left side of the body of the suture retainer.

If the two sections 66 and 68 of the suture 52 were wrapped around the body 242 of the suture retainer 244 for complete turns, the sections of the suture would be on the same side of the body 242 at the top and bottom of the suture retainer. For example, if the suture 52 was wrapped two complete turns around the body 242, the left section 66 of the suture 52 would be disposed at the left side of both the upper and lower ends of the body 242. Similarly, the right section 68 of the suture 52 could be disposed at the right side of both the upper and lower ends of the body 242 of the suture retainer.

The body 242 of the suture retainer 244 is formed as a portion of a right circular cone. The body 242 of the suture retainer 244 has an outer side surface 248 with an axially downward (as viewed in FIG. 13) and radially inward tapering configuration. The conical body 242 of the suture retainer 244 has parallel circular end surfaces 252 and 254 which extend perpendicular to a longitudinal central axis of the conical body. The circular end surfaces 252 and 254 are disposed in a coaxial relationship. The upper end surface 252 has a larger diameter than the lower end surface 254.

A pair of helical grooves 258 and 260 (FIGS. 13–16) are formed in the conical body 242. The helical grooves 258 and 260 have a spiral configuration with a central axis which is coincident with the central axis of the conical body 242. Thus, the diameter of the turns of the grooves 258 and 260 progressively decreases as the grooves extend downward (as viewed in FIG. 13) from the upper end surface 252 to the lower end surface 254. The helical grooves 258 and 260 have the same pitch.

The helical grooves 258 and 260 are wrapped in opposite directions around the conical body 242 of the suture retainer 244. Thus, as viewed from above, the helical groove 258 is wrapped in a counterclockwise direction around the body 242 of the suture retainer 244. The helical groove 260 is wrapped in a clockwise direction around the body 242 of the suture retainer 244.

The helical grooves 258 and 260 are offset by 180N. Thus, the helical groove 258 beings at the upper left (as viewed in FIG. 13) side of the body 242 and the helical groove 260 begins at the upper right side of the body 242. The entrances to the helical grooves 258 and 260 are disposed at diametrically offset locations on the circular upper end surface 252 of the body 242. The helical groove 258 ends at the lower right (as viewed in FIG. 13) side of the body 242. The helical groove 260 ends at the lower left side of the body 242. The exits from the helical grooves 258 and 260 are disposed at diametrically offset locations on the circular lower end surface 254 of the body 242. This results in the relatively large lower end surface 254 of the body 242 being disposed between the left and right sections 66 and 68 of the suture 52 and exposed to body tissue.

The groove 258 has an axially upward and radially inward sloping configuration (FIG. 14). The groove 258 has a helical open mouth or entrance 264. The groove 258 has a pair of axially upward and radially inward sloping side surfaces 266 and 268. The side surfaces 266 and 268 are interconnected by an arcuate bottom surface 270. The groove 258 has the same depth and cross sectional configuration throughout the extent of the groove.

Although only the groove 258 is illustrated in FIG. 14, it should be understood that the groove 260 has the same cross sectional configuration as the groove 258. The two grooves 258 and 260 extend between the opposite end surfaces 252 and 254 of the conical body 242. It is contemplated that the grooves 258 and 260 could have a different cross sectional configuration if desired. For example, the grooves 258 and 260 could have the cross sectional configuration shown in FIG. 11 if desired.

The grooves 258 and 260 intersect on opposite sides of the conical body 242 in the manner illustrated in FIGS. 15 and 16. At the intersections between the grooves 258 and 260, the left and right sections 66 and 68 of the suture 52 overlap (FIG. 16). The number of intersections of grooves 258 and 260 will vary as a direct function of the number of turns of the grooves 258 and 260 around the body 242.

Bridge sections 274 and 276 (FIG. 13) are provided across opposite ends of the groove 258 to facilitate in retaining the suture section 66 in the groove. Similarly, bridge sections 278 and 280 are provided across opposite ends of the groove 260 to facilitate in retaining the suture section 68 in the groove 260. If desired, the bridge sections 274, 276, 278 and 280 could be omitted.

In addition to the conical body 242, the suture retainer 244 includes a cylindrical sleeve 284 (FIG. 13). The tubular sleeve 284 has a cylindrical outer side surface 286 and a conical inner side surface 288. The inner and outer side surfaces 286 and 288 are disposed in coaxial relationship. The conical inner side surface 288 of the sleeve 284 tapers axially inward and downward (as viewed in FIG. 13) at the same angle as does the conical outer side surface 248 of the body 242.

Although the conical inner side surface 288 of the sleeve 284 has been schematically illustrated in FIG. 13 as having an inside diameter which is greater than the outside diameter of the conical body 242, it is contemplated that the conical body 242 will have substantially the same diameter as the inner side surface 288 of the sleeve 284. Therefore, when the circular end surface 252 on the conical body 242 is axially aligned with an annular end surface 292 on the sleeve 284 (as shown in FIG. 13), the outer side surface 248 on the conical body 242 will be disposed in abutting engagement with the inner side surface 288 on the sleeve 286. Of course, if the conical inner side surface 288 of the sleeve 284 has a larger diameter than the conical outer side surface 248 of the body 242, axially downward (as viewed in FIG. 13) movement of the conical body 242 relative to the sleeve 284 will result in abutting engagement between the inner side surface 288 of the sleeve and the outer side surface 248 of the conical body.

The conical body 242 and the sleeve 284 are both formed of a biodegradable polymer, such as polycaperlactone. However, the conical body 242 and the sleeve 284 could be formed of polyethylene oxide terephthalate or polybutylene terephthalate if desired. Other biodegradable or bioerodible copolymers could be utilized if desired. It is contemplated that it may be desired to form the conical body 242 and sleeve 284 of a polymer which is not biodegradable. The conical body 242 and sleeve 284 could be formed of two different materials if desired.

When the suture retainer 244 is to be positioned in a human patient's body, the left and right sections 66 and 68 of the suture are first inserted through the open center of the sleeve 284. The sections 66 and 68 of the suture 52 are then wrapped around the conical body 242 in the grooves 258 and 260. The sleeve 284 may then be moved along the suture 252 to the desired position in a patient's body.

It is believed that it will be preferred to position the left and right sections 66 and 68 of the suture 52 relative to the body tissue before winding the two sections of the suture around the body 242. However, one of the sections 66 or 68 of the suture 52 may be wound around the body 242 and inserted through the sleeve 284 before the suture is positioned relative to the body tissue. After the suture 52 has been positioned relative to the body tissue, the other section of the suture would be inserted through the sleeve 284 and wound around the body 242.

When the suture 52 has been positioned relative to the body tissue and suture retainer 244, the sections 66 and 68 of the suture 52 are tensioned as a force 296 (FIG. 13) is applied to the conical body 242. The force 296 is sufficient to cause the conical body 242 of the suture retainer 244 to slide axially along the sections 66 and 68 of the suture toward the sleeve 284. As this occurs, the outer side surface 248 on the conical body 242 moves into engagement with the inner side surface 288 on the sleeve 284. The force 296 is then effective to press the outer side surface 248 on the conical body 242 firmly against the inner side surface 288 of the sleeve.

The force 296 is also effective to press both the end surface 254 of the conical body 242 and an annular end surface 300 of the sleeve 284 against the body tissue. While the let and right sections 66 and 68 of the suture are tensioned, the force 296 is increased. After the suture retainer 244 has been pressed against the body tissue with a predetermined force 296 sufficient to cause the suture 52 to grip the body tissue with a desired tension, force applicator members, similar to the force applicator members 224, 226 and 228 of FIG. 12, compress the sleeve 284. The manner in which force is applied against the sleeve 284 is indicated schematically by arrows 302 and 304 in FIG. 13. If desired, one or more axial slot may be provided through a portion of the sleeve 284 to facilitate compression of the sleeve.

The force applied against the sleeve 284, indicated schematically at 302 and 304, causes radially inward plastic deformation of the sleeve. This force is transmitted through the sleeve to the conical body 242. The force transmitted to the conical body 242 causes a collapsing of the grooves 258 and 260. As the grooves 258 and 260 collapse, the material of the conical body 242 is plastically deformed and firmly grips or bonds to the outer side surfaces of the left and right sections 66 and 68 of the suture 52. The sleeve 284 bonds to the material of the conical body 242.

The sleeve 284 and conical body 242 of the suture retainer 244 are at a temperature below the transition temperature of the material forming the sleeve and conical body when they are compressed by the force indicated schematically at 302 and 304 in FIG. 13. This results in cold flowing of the material of both the sleeve 284 and the suture retainer 244 under the influence of the force 302 and 304. The force 302 and 304 is maintained at a predetermined magnitude for a time sufficient to result in cold plastic deformation of the material of the sleeve 284 and conical body 242. This plastic deformation or cold flow of the material of the sleeve 284 and conical body 242 occurs at a temperature which is substantially the same as the temperature of the body tissue with which the suture 52 is connected.

If desired, cold flowing of the material of the sleeve 284 and conical body 244 could be promoted by the addition of heat. Thus, the sleeve 284 and conical body 244 may be preheated before being moved into engagement with the body tissue. If desired, heat could be transmitted to the sleeve 284 and conical body 242 during application of he force 302 and 304. During the application of the force 302 and 304 to the sleeve 284, both the conical body 242 and sleeve 284 are at a temperature below the transition temperature of the material of the conical body and sleeve.

Once the suture retainer 284 has been plastically deformed to securely grip the suture 52, the suture may be knotted. Thus, a knot may be formed in the upper (as viewed in FIG. 13) end portions 66 and 68 of suture 52. The knot would pull the sections 66 and 68 of the suture firmly against the upper side surface 252 of the conical body 242. This knot would not decrease the overall force transmitting capability of the suture 52 since the suture retainer 244 would be disposed between the knot and the body tissue. Although such a knot would provide additional assurance that the suture will not work loose, it is believed that the knot is not necessary.

The tension in the suture 52 will press the annular end surface 300 on the sleeve 284 and the circular end surface 254 on the conical body 242 against the body tissue. Due to the relative large combined area of the end surfaces 254 and 300, the tension forces in the suture 52 will be applied to a relatively large area on the body tissue by the suture retainer 244. Since the suture retainer 244 applies force to a relatively large surface area on the body tissue and since the overall strength of the suture 52 is not impaired by the suture retainer 244, relatively large forces can be transmitted through the suture to the body tissue.

In the embodiment of the invention illustrated in FIGS. 13–16, the helical grooves 258 and 260 cross. This results in the left and right sections 66 and 68 of the suture 52 being disposed in overlapping engagement at the intersections between the grooves 258 and 260. The overlapping engagement of the left and right sections 66 and 68 of the suture 52 increases the resistance of the suture retainer 244 to slipping of one section of the suture relative to the other section of the suture.

Embodiments of FIGS. 17–19

In the embodiment of the invention illustrated in FIGS. 13–16, the central axis of the conical body 242 of the suture retainer 244 extends along the sections 66 and 68 of the suture 52. In the embodiments of the invention illustrated in FIGS. 17–19, a central axis of a circular body of the suture retainer extends transverse to the longitudinal axis of the suture during movement of the suture retainer toward the body tissue. Since the suture retainer of the embodiments of the invention illustrated in FIGS. 17–19 is similar to the suture retainer of the embodiment of the invention illustrated in FIGS. 13–16, similar terminology will be utilized to identify similar components. It should be understood that one or more features of the embodiments of the invention illustrated in FIGS. 1–16 may be used with the embodiments of the invention illustrated in FIGS. 17–19.

A suture retainer 312 (FIGS. 17 and 18) includes a cylindrical housing 314 and a rotatable cylinder 316. The housing 314 encloses the rotatable cylinder 316. The rotatable cylinder 316 has a central axis which is coincident with the central axis of the cylindrical housing 314.

The cylinder 316 is supported for rotation relative to the housing 314 by bearing sections 320 and 322 (FIG. 17). The bearing sections 320 and 322 are integrally formed as one piece with the housing 314. The bearing sections 320 and 322 have a conical configuration and engage conical recesses formed in opposite ends of the rotatable cylinder 316. The bearing sections 320 and 322 support the cylinder 316 in a coaxial relationship with the housing 314.

Left and right sections 66 and 68 of the suture 52 extend into the housing 314 through cylindrical openings 326 and 328. The sections 66 and 68 of the suture 52 extend from the housing 314 through openings 330 and 332. The openings 326, 328, 330 and 332 have parallel central axes which extend tangentially to the cylinder 316.

The left section 66 of the suture 52 extends through the opening 326 into the housing 314. The left section 66 of the suture 52 is wrapped in a clockwise direction (as viewed in FIG. 18) around the cylinder 316 and extends from the housing 314 through the opening 330. Similarly, the right section 68 (FIG. 17) of the suture 52 extends into the housing 314 through the opening 328. The right section 68 of the suture 52 is wrapped in a counterclockwise direction, as viewed in FIG. 18, around the cylinder 316. The turns in the left and right sections 66 and 68 in the suture 52 are axially spaced apart along the cylindrical outer side surface of the cylinder 316. If desired, helical grooves may be provided in the cylinder 316 to receive the turns of the left and right sections 66 and 68 of the suture.

The cylindrical housing 314 is formed of a biodegradable polymeric material. The cylinder 316 is also formed of a biodegradable polymeric material. However, the material of the cylinder 316 is harder than the material of the housing 314. The material of the cylinder 316 has a lower coefficient of friction than the material of the housing 314. The material of the housing 314 is easier to plastically deform than the material of the cylinder 316. Of course, the housing and cylinder 314 and 316 may be formed of the same material which may be biodegradable (polycaperlactone) or may not be biodegradable.

When the suture retainer 312 is to be positioned relative to body tissue (not shown), the left and right sections 66 and 68 of the suture are tensioned. The housing 312 is then pushed downward (as viewed in FIGS. 17 and 18) in the manner indicated schematically by an arrow 336 in FIG. 18. As this occurs, the turns or wraps of the sections 66 and 68 of the suture slide along a cylindrical outer side surface of the rotatable cylinder 316. The oppositely wound loops in the sections 66 and 68 of the suture 52 move downward along the suture toward the body tissue as the retainer 312 moves downward along the suture toward the body tissue.

Although there will be some rotational movement of the cylinder 316 relative to the housing 314, the position of the cylinder 316 relative to the housing 314 remains substantially constant during a major portion of the movement of the suture retainer 312 along the suture 52 toward the body tissue. This is because the left and right sections 66 and 68 of the suture are wrapped in opposite directions around the cylinder 316. This results in the portion of the loop in the left section 66 of the suture tending to rotate the cylinder 316 in a counterclockwise direction (as viewed in FIG. 18). At the same time, the loop formed in the right section 68 of the suture 52 tends to rotate the cylinder 316 in a clockwise direction (as viewed in FIG. 18).

Since the two sections 66 and 68 of the suture 52 tend to urge the cylinder 316 to rotate in opposite directions, the cylinder tends to remain more or less stationary relative to the housing 314. The loops in the left and right sections 66 and 68 of the suture 52 slide along the cylindrical outer side surface of the cylinder 316. However, it should be understood that there will be some rotational movement of the cylinder 316 relative to the housing 314 as the suture retainer 312 is moved toward the body tissue.

Once the housing 314 of the suture retainer 312 is moved into engagement with the body tissue, the tension is maintained in the sections 66 and 68 of the suture 52. The force 336 (FIG. 18) pressing the suture retainer 312 against the body tissue is increased. The suture retainer 312 is pressed against the body tissue with a force, indicated schematically by the arrow 336 in FIG. 18, which is sufficient to provide a desired tension in the portion of the suture 52 engaging the body tissue.

The material of the suture retainer 312 is then plastically deformed. The plastic deformation of the suture retainer 312 is accomplished by applying force against opposite sides of the housing 314 with a pair of force application members 340 and 342 (FIG. 18). The force applied against the suture retainer 312 by the force application members 340 and 342 presses the material of the housing 314 against the sections 66 and 68 of the suture and the cylinder 316 by cold flowing material of the housing.

A large gap has been shown between the cylindrical outer side surface of the cylinder 316 and a cylindrical inner side surface of the housing 314 in FIG. 18. However, it should be understood that this annular gap will be relatively small so that the material of the housing 314 can readily cold flow into engagement with the turns of the sections 66 and 68 of the suture 52 and cylinder 316. The force applied against the housing 314 also plastically deforms and causes cold flowing of the material of the cylinder 316 to provide a secure bond or grip between the material of the cylinder 316 and the suture 52.

A transducer or load cell 346 is associated with the force application member 342 and provides an output to a display unit 348. After a predetermined minimum force has been applied to the suture retainer 312 by the force application members 340 and 342 for a predetermined minimum length of time, an output from the display unit 348 to an indicator 350 activates the indicator to provide a signal that the desired plastic deformation of the suture retainer 312 has been obtained.

If desired, a knot may be tied between the left and right sections 66 and 68 of the suture 52 adjacent to a side of the housing 314 opposite from a side of the housing which is pressed against the body tissue by the suture. The knot would be pulled tight against the housing at a location between the openings 326 and 328. Since the suture retainer 312 is between the knot and the body tissue, the knot would not impair the force transmitting capability of the suture 52.

In FIGS. 17 and 18, the sections 66 and 68 of the suture 52 are wrapped in opposite directions around the cylinder 316. This results in offsetting forces being applied to the cylinder 316 by the turns in the sections 66 and 68 of the suture 52 during movement of the suture retainer 312 along the suture toward the body tissue. In FIG. 19, the left and right sections 66 and 68 of the suture 52 are wrapped in the same direction around the cylinder 316. This results in the turns or loops in the sections 66 and 68 of the suture 52 applying force to the cylinder 316 urging the cylinder to rotate in the same direction during movement of the suture retainer 312 along the sections 66 and 68 of the suture toward body tissue. Therefore, when the sections 66 and 68 of the suture 52 are wrapped in the same direction around the cylinder 316, the cylinder will freely rotate relative to the housing 314 as the suture retainer 312 is moved along the suture 52 toward the body tissue.

The overall force transmitting capability of the suture 52 is not impaired by the suture retainer 312. This is because the turns of the loops formed in the left and right sections of the suture 52 around the cylinder 316 do not form stress concentrations in the suture. If a knot had been used to interconnect the left and right sections 66 and 68 of the suture 52, in the manner taught by the prior art, the resulting stress concentration would reduce the overall force transmitting capability of the suture 52.

The cylindrical housing 314 increases the surface area on body tissue against which force is applied by tension in the suture 52 after the suture retainer 312 has been plastically deformed to grip the suture. This increases the amount of force which may be transmitted through the suture 52 without damaging the body tissue.

Figure 20:
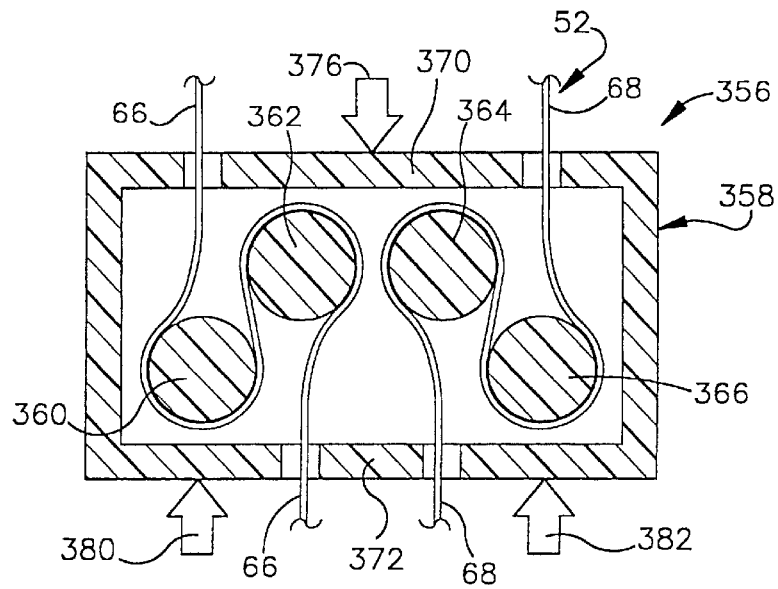
FIG. 20 is a fragmentary schematic illustration of another embodiment of the suture retainer in which a housing encloses a plurality of cylinders around which the suture is wrapped.

Embodiment of FIG. 20

In the embodiment of the invention illustrated in FIGS. 17–19, the cylinder 316 is rotatable relative to the housing 314. In the embodiment of the invention illustrated in FIG. 20, cylinders are fixedly connected with the housing. Since the embodiment of the invention illustrated in FIG. 20 is similar to the embodiment of the invention illustrated in FIGS. 17–19, similar terminology will be utilized to identify similar components. It should be understood that one or more features of the embodiments of the invention illustrated in FIGS. 1–19 may be used with the embodiment of the invention illustrated in FIG. 20.

A suture retainer 356 includes a rectangular housing 358 which encloses a plurality of cylinders 360, 362, 364 and 366. The cylinders 360–366 have parallel central axes which extend parallel to flat rectangular upper and lower side walls 370 and 372 of the housing 358. Opposite end portions of the cylinders 360–366 are fixedly connected with rectangular end walls (not shown) of the housing 358. The central axes of the cylinders 360–366 extend perpendicular to the housing end walls to which the cylinders are fixedly connected.

In the embodiment of the invention illustrated in FIG. 20, the cylinders 360–366 are formed of a biodegradable material which is relatively hard. The housing 358 is formed of a biodegradable material which is relatively soft. By forming the housing 358 of a biodegradable material which is relatively soft, plastic deformation of the housing is facilitated. The relatively hard biodegradable material forming the cylinders 360–366 has a low coefficient of friction.

Although it is preferred to form the cylinders 360–366 and housing 358 of biodegradable materials having different hardnesses, the cylinders and housing could be formed of biodegradable or nonbiodegradable materials having the same hardness if desired.

A suture 52 has left and right sections 66 and 68 which are wrapped around the cylinders 360–366 in a zig-zag fashion. Thus, the left section 66 of the suture 52 is looped around the cylinders 360 and 362. The right section 68 of the suture 52 is looped around the cylinders 364 and 366. The cylinders 360 and 362 maintain a pair of smooth, continuous bends in the left section 66 of the suture 52. Similarly, the cylinders 364 and 366 maintain a pair of smooth, continuous bends in the right section 68 of the suture 52. The smooth, continuous bends in the sections 66 and 68 of the suture 52 are free of stress inducing discontinuities. If desired, a greater or lesser number of bends could be maintained in the sections 66 and 68 of the suture 52 by a greater or lesser number of cylinders.

In the embodiment of the invention illustrated in FIG. 20, there is a single partial turn of the left section 66 of the suture around each of the cylinders 360 and 362. Similarly, there is a single partial turn of the right section 68 of the suture 52 around each of the cylinders 364 and 366. If desired, a plurality of turns or loops could be provided around each of the cylinders 360-366 by the sections 66 and 68 of the suture 52. For example, the left section 66 of the suture 52 could be wrapped for one complete revolution around the cylinder 360 and then wrapped for a partial revolution around the cylinder 360 before extending to the cylinder 362. Similarly, the right section 68 of the suture 52 could be wrapped for one complete revolution around the cylinder 366 and then wrapped for a partial revolution around the cylinder 364 before exiting from the housing 358.

After the suture 52 has been wrapped around the cylinders 360–366 in the manner illustrated schematically in FIG. 20, the suture retainer 356 is moved along the sections 66 and 68 of the suture 52 toward body tissue. As the housing 358 is moved downward (as viewed in FIG. 20), toward the body tissue, the left and right sections 66 and 68 of the suture 52 slide along the outer side surfaces of the cylinders 360–366. As this occurs, the cylinders 360–366 cooperate to maintain a plurality of bends in each of the sections 66 and 68 of the suture 52.

Once the housing 358 has been pressed against the body tissue with a predetermined force 376 while a predetermined tension is maintained in the left and right sections 66 and 68 of the suture 52, the housing 358 is plastically deformed to grip the suture 52. Thus, force, indicated by arrows 380 and 382 in FIG. 20 supplied against a side of the housing 358 opposite from the force 376. This force is effective to plastically deform the material of the housing and to press the material of the housing against the cylinders 360–366 and against the sections 66 and 68 of the suture 52.

As the forces indicated by the arrows 376, 380 and 382 plastically deform the housing 358, the material of the housing cold flows under the influence of the force. This cold flow of the material of the housing results in the left and right sections 66 and 68 of the suture being firmly pressed against the cylinders 360–366 to form a solid bond with the left and right sections 66 and 68 of the suture 52. Since the material forming the cylinders 360–366 is relatively hard, compared to the material forming the housing 358, the housing will deform to a greater extent than the cylinders during cold flow of the material of the housing. However, there will be some plastic deformation of the cylinders 360–366.

The force transmitting capability of the suture 52 is enhanced by minimizing stress concentrations in the suture and by transmitting force from the housing 358 to a large area on the body tissue. The bends formed in the suture 52 around the cylinders 360–366 are free of abrupt stress inducing discontinuities. The housing 358 transmits force to the body tissue located between the opposite sides of the left and right sections 66 and 68 of the suture 52. Therefore, stress concentrations in both the body tissue and the suture 52 tend to be minimized. If desired, a knot may be tied between the upper (as viewed in FIG. 20) end portions of the left and right sections 66 and 68 of the suture 52. Although such a knot would provide additional assurance that the suture 52 will not work loose, it is believed that the knot will not be necessary.

One of the ends of the suture could be fixedly connected with the housing 358. This could be done by forming the suture 52 as one piece with the housing 358 or by using a fastener. If one end of the suture is fixedly connected with the housing 358, one of the sets of cylinders, for example, the cylinders 360 and 362, could be eliminated.

Figure 21:
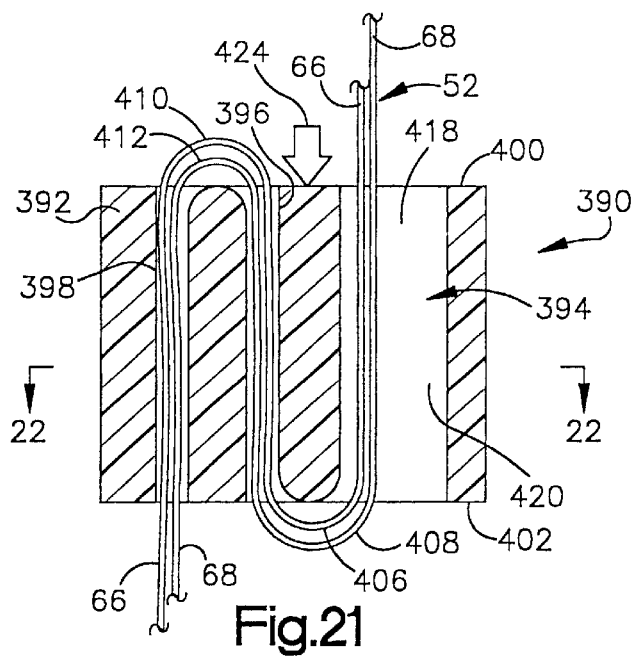
FIG. 21 is a schematic illustration depicting the manner in which the suture zig-zags through passages in another embodiment of the suture retainer.
Figure 22:
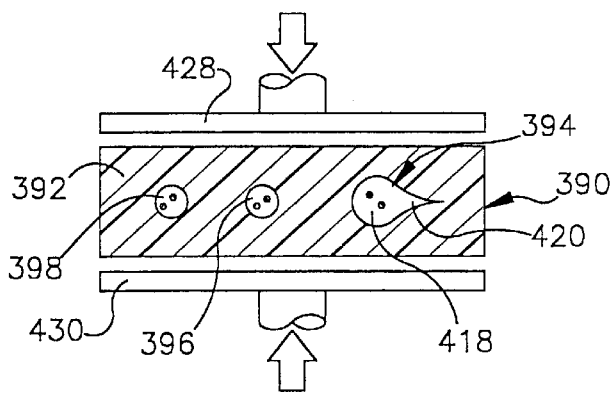
FIG. 22 is a schematic sectional view, taken generally along the line 22—22 of FIG. 21, further illustrating the manner in which the suture extends through the suture retainer.

Embodiment of FIGS. 21–22

In the embodiments of the invention illustrated in FIGS. 9–20, bends are formed in the left and right sections 66 and 68 of the suture 52 by circular surfaces. In the embodiment of the invention illustrated in FIGS. 21 and 22, the bends are formed in the suture by passages through a rectangular member. Since the embodiment of the invention illustrated in FIGS. 21 and 22 is similar to the embodiment of the invention illustrated in FIGS. 9–20, similar terminology will be utilized to identify similar components. It should be understood that one or more of the features of the embodiments of the invention illustrated in FIGS. 1–20 may be used with the embodiment of the invention illustrated in FIGS. 21–22.

A suture retainer 390 is formed in a single rectangular piece of biodegradable material. The suture retainer 390 includes a rectangular body 392 formed of a suitable biodegradable material. However, the rectangular body 392 could be formed of a non-biodegradable material if desired.

A plurality of parallel passages 394, 396 and 398 extend between opposite parallel rectangular end surfaces 400 and 402 of the body 392. The left and right sections 66 and 68 of the suture 52 zig-zag through the passages 394, 396 and 398 in a side-by-side relationship. The sections 66 and 68 of the suture 52 zig-zag through the passages 394, 396 and 398 to form a series of bends in the suture.

The passages 394, 396 and 398 in the body 392 of the suture retainer 390 cooperate to form smooth, continuous bends 406, 408, 410 and 412 (FIG. 21) in the sections 66 and 68 of the suture 52. Thus, the left and right sections 66 and 68 of the suture 52 extend through the straight passage 394. Bends 406 and 408 are formed in the portions of the sections 66 and 68 of the suture disposed between the passage 394 and the passage 396. Similarly, bends 410 and 412 are formed in the sections 66 and 68 of the suture 52 disposed between the passages 396 and 398. Of course, if there were additional passages formed in the rectangular body 392, additional bends would be formed in the suture 52.

The bends 406–412 in the sections 66 and 68 of the suture 52 are smooth and free of stress inducing discontinuities. By keeping the suture 52 free of stress inducing discontinuities, the force which can be transmitted through the suture tends to be maximized. If a knot was substituted for the suture retainer 390, stress concentrations would be formed and the force transmitting capability of the suture reduced.

The passage 394 has a main section 418 and a gripping section 420. The gripping section 420 has a tapered configuration (FIG. 22) and extends sideward from the main section 418. The left and right sections 66 and 68 of the suture 52 may be pulled from the main section 418 of the passage 394 into the gripping section 420 of the passage. As this occurs, the side surfaces of the passage 394 grip opposite sides of the left and right sections 66 and 68 of the suture 52 to hold the left and right sections of the suture against axial movement relative to the rectangular body 392 of the suture retainer 390.

The suture retainer 390 is formed of a single piece of biodegradable material, such as polycaperlactone. Of course, other suitable biodegradable or bioerodible materials could be utilized if desired. It is contemplated that the suture retainer 390 could be formed of materials which do not biodegrade.

After the suture 52 has been inserted into the suture retainer 390, in the manner illustrated schematically in FIG. 21, the suture retainer is moved along the suture toward body tissue (not shown). As the suture retainer 390 is moved along the suture 52, the side-by-side sections 66 and 68 of the suture slide in the same direction on surfaces of the suture retainer 390.

To effect movement of the suture retainer 390 along the suture 52, force is applied against the body 392, in the manner indicated schematically by an arrow 424 in FIG. 21. This causes the body 392 of the suture retainer 390 to slide along the sections 66 and 68 of the suture 52. At this time, the left and right sections 66 and 68 of the suture are tensioned. Therefore, the left and right sections of the suture slide along surfaces of the passages 394, 396 and 398 as the rectangular body 392 of the suture retainer 390 is moved toward the body tissue. As this occurs, the bends 406–412 move along the sections 66 and 68 of the suture 52 toward the body tissue.

When the leading end surface 402 on the rectangular body 392 of the suture retainer 390 engages the body tissue, the force indicated schematically by the arrow 424 is increased to a predetermined force. As this occurs, a predetermined tensioning force is applied to the left and right sections 66 and 68 of the suture 52. This results in the suture 52 being pulled tight to grip the body tissue with a desired force. The rectangular end surface 402 on the body 392 of the suture retainer 390 distributes the tension force in the suture 52 over a relatively large area on the body tissue.

While the retainer body 392 is being pressed against the body tissue with the predetermined force and the left and right sections 66 and 68 of the suture 52 are pulled taut with a predetermined tensioning force, the left and right sections 66 and 68 of the suture may be pulled towards the right (as viewed in FIGS. 21 and 22). As this occurs, the left and right sections 66 and 68 of the suture 52 will move from the main section 418 of the passage 394 into the gripping section 420 of the passage. This results in a frictional grip between the retainer body 392 and the suture 52 to hold the suture against movement relative to the retainer body and to maintain the desired tension in the suture.

While the body 392 of the suture retainer 390 is being pressed against the body tissue with the predetermined force 424 and while the predetermined tension is maintained in the left and right sections 66 and 68 of the suture 52, the material of the suture retainer 390 is plastically deformed. To plastically deform the material of the suture retainer 390, force applying members 428 and 430 (FIG. 22) apply a predetermined force against opposite sides of the body 392 of the suture retainer. This force causes cold flowing of the material of the body 392 of the suture retainer.

As the plastic deformation of the body 392 of the suture retainer 390 occurs, the passages 394, 396 and 398 are collapsed and the material of the body 392 of the suture retainer 390 cold flows around and grips the left and right sections 66 and 68 of the suture 52. The plastic deformation of the body 392 of the suture retainer 390 occurs at a temperature below the transition temperature of the material forming the suture retainer. If desired, the suture retainer 390 could be heated to promote cold flow of the material of the suture retainer.

In the embodiment of the invention illustrated in FIGS. 21 and 22, the gripping section 420 mechanically grips a portion of the suture 52. If desired, the gripping section 420 could be eliminated and the suture moved into engagement with a projection from the body 392. The upper (as viewed in FIG. 21) portions of the suture 52 could be wrapped around a projection from the body 392. Alternatively, the upper (as viewed in FIG. 21) portions of the suture could be moved into engagement with one or more hook-shaped locking notches on the body 392 of the suture retainer 390.

Embodiments of FIGS. 23–25

In the embodiment of the invention illustrated in FIGS. 21 and 22, the left and right sections 66 and 68 of the suture 52 extend through the passages 394, 396 and 398 in a side-by-side relationship. In the embodiments of the invention illustrated in FIGS. 23–25, loops are formed in the left and right sections of the suture around portions of the suture retainer. Since the embodiments of the invention illustrated in FIGS. 23–25 is similar to the embodiment of the invention illustrated in FIGS. 21–22, similar terminology will be utilized to identify similar components. It should be understood that one or more features of the embodiments of the invention illustrated in FIGS. 1–22 could be used with the embodiments of the invention illustrated in FIGS. 23–25.

A suture retainer 440 (FIG. 23) has a rectangular body 442. A plurality of straight parallel cylindrical passages 444, 446 and 448 extend between flat parallel rectangular end surfaces 450 and 452 of the rectangular body 442 of the suture retainer 440. The left and right sections 66 and 68 of the suture 52 extend through the passages 444, 446 and 448 in a zig-zag manner.

The left section 66 of the suture 52 zig-zags through the passages 444, 446 and 448 in the rectangular body 442 of the suture retainer 440. When the left section 66 of the suture 52 is inserted into the suture retainer 440, the left section 66 of the suture is first moved downward (as viewed in FIG. 23) through passage 448. A smooth, continuous first bend 456 is then formed in the left section 66 of the suture 52 and the left section is moved upward through the passage 446. A smooth, continuous second bend 458 is then formed in the left section 66 of the suture 52. The left section 66 of the suture 52 is then moved downward through the passage 444.

The right section 68 of the suture 52 is also inserted into the suture retainer 440 in a zig-zag fashion. Thus, the right section 68 of the suture 52 is moved downward through the passage 444. A smooth, continuous first bend 462 is formed in the right section 68 of the suture 52. The right section 68 of the suture 52 is then moved upward through the passage 446. A smooth, continuous second bend 464 is then formed in the right section 68 of the suture 52. The right section 68 of the suture 52 is then moved downward through the passage 448.

In the embodiment of the invention illustrated in FIG. 23, the left and right sections 66 and 68 of the suture 52 are not aligned or in a side-by-side relationship with each other. Thus, the bends 456 and 458 in the left section 66 of the suture 52 are offset from the bends 462 and 464 in the right section 68 of the suture 52. The bends 456, 458, 462, and 464 are free of stress inducing discontinuities which would tend to weaken the suture 52.

After the suture 52 has been inserted into the suture retainer 440, in the manner illustrated schematically in FIG. 23, the left and right sections 66 and 68 of the suture are tensioned and force is applied to the rectangular body 442 of the suture retainer 440 to move the suture retainer along the suture 52 toward the body tissue. As this occurs, the left and right sections 66 and 68 of the suture 52 slide in opposite directions along the surfaces of the passages 444, 446 and 448. As this occurs, the zig-zag portion of the suture 52 is moved along the suture toward the body tissue.

When the rectangular leading end surface 452 of the body 442 of the suture retainer 440 moves into engagement with the body tissue, the suture retainer is pressed against the body tissue with a predetermined force while maintaining a predetermined tension in the left and right sections 66 and 68 of the suture. The suture retainer 440 is then plastically deformed to grip the left and right sections 66 and 68 of the suture 52. To plastically deform the material of the suture retainer 440, force is applied against opposite sides of the suture retainer 440, in the manner indicated by arrows 470 and 472 in FIG. 23.

The force indicated by the arrows 470 and 472 causes cold flow of the material of the suture retainer 440. The suture retainer 440 is formed from a single piece of biodegradable polymeric material, such as polycaperlactone. The plastic deformation of the suture retainer 440 occurs while the material of the suture is a temperature which is below the transition temperature of the material and is at a temperature close to the temperature of the body tissue. If desired, the suture retainer 440 could be heated to a temperature above the temperature of the body tissue and below the transition temperature of the material of the suture retainer to promote cold flow of the material of the suture retainer.

In the embodiment of the invention illustrated in FIG. 24, the sections of the suture 52 are wrapped around portions of the suture retainer in smooth, continuous loops. Thus, in the embodiment of the invention illustrated in FIG. 24, a suture retainer 480 includes a rectangular body 482 formed of a biodegradable polymeric material. A plurality of straight cylindrical passages 484, 486 and 488 extend between and are perpendicular to flat parallel end surfaces 492 and 494 on the rectangular body 482 of the suture retainer 480.

The suture 52 includes left and right sections 66 and 68. The left and right sections 66 and 68 are wrapped, in zig-zag fashion, around portions 498 and 500 of the rectangular body 482. This results in the formation of left and right loops 502 and 504 in the left and right sections 66 and 68 of the suture 52. The loops 502 and 504 are free of stress inducing discontinuities.

When the suture retainer 480 is to be positioned relative to the body tissue of a human patient, the left and right sections 66 and 68 of the suture 52 are tensioned with a predetermined force. Force is then applied to the rectangular body 482 of the suture retainer to move the suture retainer downward (as viewed in FIG. 24) along the suture 52. As this occurs, the left and right sections 66 and 68 slide along surfaces of the passages 484, 486 and 488. In addition, the loops 502 and 504 move downward (as viewed in FIG. 4) along the suture 52.

The leading end surface 494 of the rectangular body 482 is pressed against the body tissue with a predetermined force while a predetermined tension is maintained in the left and right sections 66 and 68 of the suture 52. The material of the suture retainer 480 is then plastically deformed to grip the left and right sections 66 and 68 of the suture 52. When the material of the suture retainer 480 is plastically deformed, the material of the suture retainer is below its transition temperature and is at a temperature close to the temperature of the body tissue. Therefore, the material of the suture retainer 480 cold flows under the influence of force applied against the suture retainer to collapse the passages 484, 486 and 488 and grip the left and right sections 66 and 68 of the suture 52.

The flat rectangular end surfaces of the suture retainer 480 applies force over a relatively large surface area on the body tissue. This reduces any tendency for the suture 52 to cut or separate the body tissue. The force which can be transmitted through the suture 52 is maximized by eliminating sharp bends in the suture. If the suture retainer 480 was eliminated and the suture was secured with a knot, the suture would be weakened by stress concentrations formed at sharp bends in the knot.

In the embodiment of the invention illustrated in FIG. 25, a suture retainer 510 includes a rectangular body 512 formed of a biodegradable polymeric material. A plurality of straight parallel cylindrical passages 514, 516, 518, and 520 extend between flat rectangular end surfaces 522 and 524 of the body 512.

The suture 52 includes left and right sections 66 and 68. Separate left and right loops 530 and 532 (FIG. 25) are formed in the sections 66 and 68 of the suture 52. Thus, the left loop 530 in the left section 66 of the suture 52 extends through the passages 518 and 520 in the rectangular body 512 of the suture retainer 510. Similarly, the right loop 532 extends through the passages 514 and 516 in the rectangular body 512 of the suture retainer 510.

When the suture retainer 510 is to be positioned relative to body tissue, the left and right sections 66 and 68 of the suture 52 are tensioned. Force is then applied to the suture retainer 510 to move the suture retainer downward (as viewed in FIG. 25) along the suture 52 into engagement with the body tissue. After the lower end surface 524 of the rectangular body 512 of the suture retainer 510 has been pressed against the body tissue with a predetermined force, the biodegradable polymeric material of the suture retainer 510 is plastically deformed by applying force against the suture retainer and cold flowing the material of the suture retainer. Cold flow of the material of the body 512 collapses the passages 514–520. The material of the body 512 then firmly grips the suture 52.

After plastic deformation of the material of the body 512, the suture retainer 510 at a temperature below the transition temperature of the material, a knot may be tied between the upper portions of the suture. This knot would be pressed tightly against the upper end surface 522 of the rectangular body 512 of the suture retainer 510. This know would be disposed at a location between the locations of the passages 516 and 518 before plastic deformation of the body 512 of the suture retainer 510. It is believed that such a knot may not be necessary.

In the embodiment of the invention illustrated in FIGS. 24 and 25, the passages through the rectangular bodies of the suture retainer are shorter than the passages through the rectangular body of the suture retainer illustrated in FIG. 23. However, it should be understood that the passages through the rectangular bodies of the suture retainers illustrated in FIGS. 24 and 25 could have a longer length if desired.

In the embodiments of the invention illustrated in FIGS. 23–25, the suture 52 is separate from the suture retainers 440, 480 and 510. However, one end of the suture 52 could be connected with any one of he suture retainers 440, 480 and 510. If this was done only one of the sections 66 or 68 would be zig-zagged through passages in a suture retainer. For example, an end of the left section 66 of the suture 52 may be fixedly connected with one of the suture retainers 440, 480 or 510. Only the right section 68 of the suture 52 would have to be inserted through the passages in the one suture retainer 440, 480 or 510. The end of the suture 52 could be fixedly connected with a suture retainer 440, 480 or 5110 by a suitable fastener or by forming the suture as one piece with the suture retainer.

Figure 26:
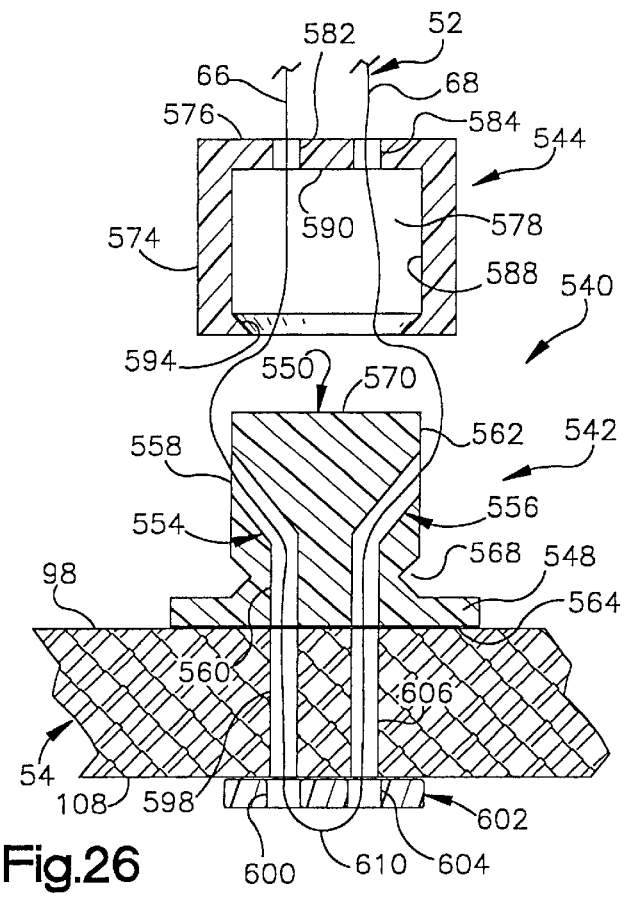
FIG. 26 is a schematic sectional view illustrating the manner in which a two-section embodiment of the suture retainer is positioned relative to body tissue prior to engagement of the two sections of the suture retainer.
Figure 27:
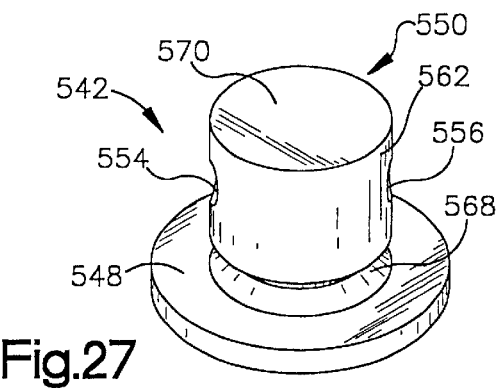
FIG. 27 is a pictorial illustration of an inner or lower section of the suture retainer of FIG. 26.
Figure 28:
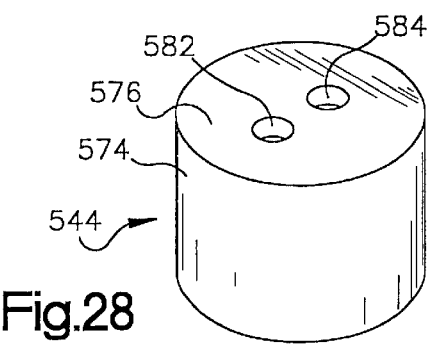
FIG. 28 is a pictorial illustration of an outer or upper section of the suture retainer of FIG. 26.

Embodiment of the Invention Illustrated in FIGS. 26, 27 and 28

In the embodiment of the invention illustrated in FIGS. 21–25, the suture retainer is formed form a single piece of biodegradable polymeric material. In the embodiment of the invention illustrated in FIGS. 26–28, the suture retainer is formed from a plurality of pieces of biodegradable polymeric material. Since the embodiment of the invention illustrated in FIGS. 26–28 is similar to the embodiment of the invention illustrated in FIGS. 21–25, similar terminology will be utilized to identify similar components. It should be understood that one or more of the features of the embodiments of the invention illustrated in FIGS. 1–25 could be used with the embodiment of the invention illustrated in FIGS. 26–28. A suture retainer 540 (FIG. 26) includes a base 542 (FIGS. 26 and 27) and a sleeve or cap 544 (FIGS. 26 and 28). The base 542 has a circular flange 548 which extends radially outward from an upstanding central or post portion 550 (FIGS. 26 and 27). The post portion 550 has a generally cylindrical configuration and is disposed in a coaxial relationship with the circular flange 548. The flange 548 and post portion 550 are integrally formed from one piece of a biodegradable material, such as polycaperlactone. However, the base 542 and/or the cap 544 could be formed of a material which is not biodegradable.

A pair of passages 554 and 556 are provided in the post portion 550. The passage 554 includes a radially inward and downward sloping entrance portion 558 and a main portion 560. The main portion 560 extends parallel to the longitudinal central axis of the post portion 550. The entrance portion 558 of the passage 554 extends inwardly from a cylindrical outer side surface 562 of the post portion 550. The main portion 560 of the passage 554 extends perpendicular to a flat circular bottom side surface 564 of the flange 548.

The passage 556 has the same configuration as the passage 554. The passage 556 is disposed diametrically opposite to the passage 554. The passages 554 and 556 have a nonlinear configuration and form bends in he left and right sections 66 and 68 of the suture 52. The passages 554 and 556 are circumscribed by an annular recess 568 which extends around the lower end of the post portion 550 adjacent to the flange 548.

The upper end of the post portion 550 has a flat circular side surface 570 (FIG. 27). The flat side surface 570 on the post portion 550 extends parallel to and is coaxial with the flat bottom side surface 564 (FIG. 26) on the flange 548. The annular recess 568 is coaxial with the flange 548. The base portion 542 is formed of a biodegradable material, such as polycaperlactone. Other polymers which are biodegradable or bioerodible may be used. It is also contemplated that the base portion 542 could be formed of a polymer which does not biodegrade, such as an acetyl resin.

In addition to the base portion 542, the suture retainer 540 includes the one piece, cylindrical cap or sleeve 544 (FIG. 28). The cap 544 has a cylindrical outer side surface 574. A circular end surface 576 extends radially inwardly from the side surface 547. The cap 544 has a cylindrical cavity 578 (FIG. 26) which is disposed in a coaxial relationship with the cylindrical outer side surface 574 and end surface 576.

A pair of cylindrical passages 582 and 584 extend between the cavity 578 and the circular end surface 576 of the cap 544 (FIG. 26). The cavity 578 has a cylindrical side surface 588 which is disposed in a coaxial relationship with the outer side surface 574 on the cap 544. In addition, the cavity 578 has a circular end surface 590 which extends parallel to and is coaxial with the outer end surface 576 on the cap 544 (FIG. 26). An annular rib 594 (FIG. 26) projects radially inward from the cylindrical inner side surface 588 of the cavity 578. The cap 544 is integrally formed as one piece of a suitable biodegradable polymeric material, such as polycaperlactone. However, the cap 544 may be formed of a material which is not biodegradable.

When the suture 52 is to be connected with body tissue 54 (FIG. 26), one of the sections of the suture, for example, the right section 68, is threaded through the passage 582 into the cavity 578 in the cap 544. At this time, the suture 52 extends away from the cap 544 so that the left section 66 of the suture is disposed at a remote location. The right section 68 of the suture is then threaded through the passage 554 in the base portion 542. The right section 68 of the suture 52 is then threaded through a passage 598 in the body tissue 54.

In addition, the right section 68 of the suture 52 is threaded through a passage 600 in a force distribution member or button 602 which engages a lower side of the body tissue 54. The suture 52 is then threaded through a second passage 604 in the button 602 and a passage 606 in the body tissue 54. The button 602 distributes tension forces in the suture 52 over a relatively large area on the lower (as viewed in FIG. 26) side 108 of the body tissue. However, the button 602 could be omitted if desired.

The right section 68 of the suture is then threaded upward (as viewed in FIG. 26) through the passage 556 in the base portion 542 and into the cavity 578 in the cap 544. The right section 68 of the suture 52 is threaded out of the cavity 568 through the passage 584. As this occurs, the left section 66 of the suture 52 is pulled into the cap 544 and base portion 542.

Once the suture 52 has been threaded through the base portion 542 and cap 544 in the manner previously explained, the sections 66 and 68 of the suture are tensioned and the base portion 542 is slid along the suture 52. As this occurs, the bends formed in the left and right sections 66 and 68 of the suture 52 by the passages 554 and 556 in the base portion 542 are moved along the suture toward the body tissue 54. The bottom side surface 564 of the base portion 542 is then pressed against an upper side surface 98 of the body tissue 54 in the manner illustrated in FIG. 26.

The flat circular bottom side surface 564 of the flange 548 transmits force from the suture 52 to a relatively large area on the surface 98 of the body tissue 54. At this time, the tension in a connector portion 610 of the suture 52 will pull the force distribution member or button 602 firmly upward against a lower side surface 108 of the body tissue 54. This results in the body tissue 54 being clamped between the relatively large bottom surface area on the flange 548 and the button 602.

While the tension is maintained in the left and right sections 66 and 68 of the suture 52, the cap 544 is slid downward along the suture 52 into engagement with the base portion 542. Further downward movement of the sleeve or cap 544 resiliently deflects the rib 594 radially outward. Continued downward movement (as viewed in FIG. 26) of the sleeve or cap 544 moves the rib 594 along the outer side surface 562 of the post portion 542 into alignment with the recess 568. As this occurs, the rib 594 snaps into the recess 568.

Once the rib 594 is snapped into the recess 568, the left and right sections of the suture 52 are firmly gripped between the cylindrical inner side surface 588 of the cavity 578 in the cap 544 and the cylindrical outer side surface 562 of the post portion 550. In addition, the left and right sections 66 and 68 of the suture 52 are gripped between the circular end surface 590 of the cavity 578 and the circular end surface 570 of the post portion 550. The cap 544 and post portion 550 cooperate to form bends in the left and right sections 66 and 68 of the suture.

Under certain circumstances, it is believed that the mechanical gripping action provided between the cap 544 and base portion 542 of the suture retainer 540 may be sufficient to hold the suture 52 against movement relative to the body tissue. However, it is believed that it will be preferred to enhance the grip of the suture retainer 540 on the suture 52 by plastically deforming the material of the suture retainer. The plastic deformation of the suture retainer 540 occurs with the suture retainer at a temperature which is below the transition temperature of the biodegradable polymeric material forming the base portion 542 and cap 544 of the suture retainer.

Plastic deformation of the base portion 542 and cap portion 544 of the suture retainer 540 is accomplished by applying force against the cylindrical outer side surface 574 of the cap 544 in the same manner as illustrated schematically in FIG. 12. The force applied against the cylindrical outer side surface 574 (FIG. 26) of the cap 544 causes the material of the cap to cold flow and press against the left and right sections 66 and 68 of the suture 52. As this occurs, the passages 554 and 556 in the base portion 542 collapse. Due to the bends provided in the left and right sections 66 and 68 of the suture 52 in passing through the passages 554 and 556, and around the outside of the post portion 550 of the base portion 542, there is an extremely secure gripping action of the suture 52 upon plastic deformation of material of the cap 544 and base portion 542.

The force applied against the outer side surface 574 of the cap 544 is sufficient to cause cold flow of the material of the cap 544 and post portion 550. Cold flow of the material of the cap 544 firmly clamps the sections 66 and 68 of the suture 52 between the cap and post portion 550. Cold flow of the material of the post portion 550 collapses the passages 554 and 556. This results in a cold bonding of the material of the post portion 550 with the suture 52. The suture 52 is then securely gripped by the post portion 554.

It is preferred to form the base portion 542 and the cap 544 of the suture retainer 540 of the same biodegradable polymeric material. However, the base portion 542 could be formed of a biodegradable material which is somewhat harder than the biodegradable material forming the cap 544. This would facilitate plastic deformation of the cap 544 under the influence of force applied against the outer side surface 574 of the cap. If desired, the base portion 542 and/or cap 544 could be formed of a material which does not biodegrade.

After the suture retainer 540 has been plastically deformed by cold flowing the material of the suture retainer, the suture 52 may be knotted. Thus, a knot may be tied to interconnect the left and right sections 66 and 68 of the suture 52 in a known manner. During the tying of this knot, the suture 52 is pulled taut against the end surfaces 576 on the cap 544. The knot will be disposed between the passages 582 and 584 in the cap 544. The knot will not reduce the overall force transmitting capability of the suture 52 since the suture retainer 540 will be disposed between the knot and the body tissue 54. Although such a knot may be provided to be certain that the suture 52 does not work loose under the influence of varying loads, it is believed that the suture retainer 540 will be very capable of holding the suture 52 without the additional protection provided by the knot.

Embodiment of FIG. 29

In the embodiment of the invention illustrated in FIGS. 13–16, the suture 52 is wrapped around a conical body 242 which is moved into a sleeve 284 of a suture retainer 244. In the embodiment of the invention illustrated in FIG. 29, the suture extends through passages formed in a conical body and a sleeve. Since the embodiment of the invention illustrated in FIG. 29 is similar to the embodiment of the invention illustrated in FIGS. 13–16, similar terminology will be utilized to identify similar components. It should be understood that one or more of the features of the embodiments of the invention illustrated in FIGS. 1–28 could be used with the embodiment of the invention illustrated in FIG. 29.

A suture retainer 622 includes a conical body 624 and a cylindrical sleeve or base 626. The conical body 624 has an outer side surface 628 which is formed as a portion of a right circular cone. The outer side surface 628 of the conical body 624 extends between flat parallel circular end surfaces 630 and 632. The end surfaces 630 and 632 are disposed in a coaxial relationship with each other and with the outer side surface 628 of the conical body 624. The end surface 632 of the conical body 624 has a diameter which is smaller than the diameter of the end surface 630 of the conical body.

A pair of cylindrical passages 636 and 638 are disposed in the conical body 624. The passages 636 and 638 have straight central axes which are skewed at an acute angle to the central axis of the conical body 624. If desired, the passages 636 and 638 could have nonlinear central axes to promote the forming of bends in the suture 52. For example, the passages 636 and 638 could have a helical configuration. The conical body 624 is formed from a single piece of a biodegradable polymeric material, such as polycaperlactone.

The cylindrical sleeve 626 has a cylindrical outer side surface 642. The side surface 642 extends between a flat annular end surface 644 and a circular end surface 646. The end surfaces 644 and 646 extend parallel to each other and are disposed in a coaxial relationship.

A recess 650 is formed in the cylindrical sleeve 626. The recess 650 is of the same size and configuration as the conical body 624. The recess 650 has a side wall 652 which is formed as a portion of a cone. In addition, the recess 650 has a circular end surface 654 which extends parallel to the outer end surface 646 on the sleeve 626. The side wall 652 of the recess 650 has the same angle of taper as the outer side surface 628 of the conical body 624. However, if desired, the taper in the side wall 652 of the recess 650 could be slightly less than the taper in the outer side surface 628 of the conical body 624 to promote a wedging action between the conical body and the sleeve 626.

A pair of parallel cylindrical passages 660 and 662 extend between and are perpendicular to the end wall 654 of the recess 650 and the end surface 646 on the sleeve 626. The passages 660 and 662 have a linear configuration. However, the passages 660 and 662 could have a nonlinear configuration if desired.

When the suture retainer 622 is to be positioned relative to body tissue, the left section 66 of the suture 52 is inserted through the passage 660 in the sleeve 626. The left section 66 of the suture 52 is then inserted through the passage 636 in the conical body 624. Similarly, the right section 68 of the suture 52 is inserted through the passage 662 in the sleeve 626 and the passage 638 in the conical body 624.

The left and right sections 66 and 68 of the suture 52 are then tensioned and the sleeve 626 is moved along the suture 52 into engagement with the body tissue. When the end surface 646 of the sleeve has engaged the body tissue, the force applied against the sleeve and tension in the sections 66 and 68 of the suture 52 are increased. While a predetermined force is applied against the sleeve 626, the conical body 624 is moved along the left and right sections 66 and 68 of the suture 52 into the recess 650 in the sleeve. As this occurs, the left and right sections 66 and 68 of the suture are clamped between the outer side surface 628 of the conical body 624 and the conical side wall 652 of the recess 650.

To enhance the gripping action between the conical body 624 and the sleeve 626, force is applied against the cylindrical outer side surface 642 of the sleeve in the same manner as indicated schematically in FIG. 12. This force causes plastic deformation of the material of the sleeve 626 to firmly grip the conical body 624 and the left and right sections 66 and 68 of the suture 52. The force applied against the outer side surface 642 of the sleeve 626 causes a cold flowing of the material of the sleeve 626. The cold flowing of the material of the sleeve 626 will collapse the passages 660 and 662 to firmly grip the portion of the left and right sections 66 and 68 of the suture 52 extending through the passages.

In addition, the force applied against the sleeve 626 will be sufficient to cause plastic deformation, that is, cold flowing, of the material of the conical body 624 to collapse the passages 636 and 638. This results in the portions of the left and right sections 66 and 68 of the suture 52 disposed in the passages 636 and 638 being firmly gripped by material of the conical body 624.

It is contemplated that one end of the suture 52 could be fixedly connected with the suture retainer 622. Thus, one end of the suture 52 could be fixedly connected with the conical body 624. Alternatively, one end of the suture 52 could be fixedly connected with the sleeve 626.

It is also contemplated that a knot could be tied between the left and right sections 66 and 68 of the suture 52 at a location above (as viewed in FIG. 92) the suture retainer. The knot would be tied adjacent to the end surface 650 on the conical body 624. The knot would be tied immediately after plastically deforming the material of the suture retainer. It should be understood that the suture retainer 622 should be more than adequate to hold the suture 52 and the knot may be omitted.

The use of the suture retainer 622, rather than forming a knot to interconnect the two sections 66 and 68 of the suture 52, increases the force transmitting capability of the suture 52. This is because the stress concentrations induced by the forming of a knot are avoided.

In addition, the use of the suture retainer 62, rather than forming a knot to interconnect the two sections 66 and 68 of the suture 52, reduces stress concentrations in the body tissue. The flat end surface 646 distributes tension forces in the suture 52 over a relatively large surface area on the body tissue. This minimizes stress concentrations in the body tissue and minimizes any tendency for the body tissue to be cut or separated by the force applied against the body tissue.

Embodiment of FIGS. 30 and 31

In the embodiment of the invention illustrated in FIG. 29, the left and right sections 66 and 68 of the suture 52 are inserted into passages formed in the conical body 624. In the embodiment of the invention illustrated in FIGS. 30 and 31, the conical body 34 has a hinge section which is pivotal to open the conical body and facilitate insertion of the left and right sections of the suture. Since the embodiment of the invention illustrated in FIGS. 30 and 31 is similar to the embodiment of the invention illustrated in FIG. 29, similar terminology will be utilized to identify similar components. It should be understood that one or more of the features of the embodiments of the invention illustrated in FIGS. 1–92 could be used with the embodiment of the invention illustrated in FIGS. 30 and 31. A suture retainer 670 (FIG. 30) includes a conical body 672 and a sleeve 674. The conical body 672 is formed as two sections 676 and 678 (FIG. 31). The sections 676 and 678 of the conical body are pivotally interconnected at a hinge 680. The hinge 680 is integrally formed as one piece with the sections 676 and 678 of the conical body 672. The hinge 680 enables the left and right sections 66 and 68 (FIG. 30) of the suture 52 to be inserted through an opening 684. The opening 684 extends between axially opposite ends of the conical body 672.

The sleeve 674 includes a circular flange 688 which extends radially outward from a cylindrical outer side surface 690 of the sleeve 674. A conical recess 692 has a relatively large open end in an upper annular end surface 694 of the sleeve 674 and a relatively small open end in a flat annular end surface 696 disposed on the bottom of the flange 688.

The left and right sections 66 and 68 of the suture are inserted through the open ended conical recess 692 in the sleeve 674. The left and right sections 66 and 68 of the suture 52 are then inserted through the opening 684 (FIG. 31) into the conical body 672.

While tension is maintained in the left and right sections 66 and 68 of the suture 52, the sleeve 674 is moved along the suture until the leading end surface 696 on the bottom of the flange 688 engages the body tissue. The sleeve 674 is then pressed against the body tissue with a predetermined force while a predetermined tension is maintained in the left and right sections 66 and 68 of the suture 52. The conical body 672 is then moved along the left and right sections 66 and 68 of the suture 52 into the open ended recess 692 in the sleeve 674.

Force is then applied against the outer side surface 690 of the sleeve 674 to plastically deform the sleeve. As this occurs, the material of the sleeve 674 cold flows radially inward and applies force against the conical body 672. This force is sufficient to cause cold flowing of the material of the conical body and gripping of the left and right sections 66 and 68 of the suture 52 with the material of the conical body 672.

The conical body 672 and sleeve 674 are formed of a biodegradable material. However, the conical body 672 and/or sleeve 674 could be formed of a different material if desired.

Embodiment of FIGS. 32 and 33

In the embodiment of the invention illustrated in FIGS. 29, 30 and 31, two-piece suture retainers are utilized to grip the left and right sections of the suture 52. In the embodiment of the invention illustrated in FIGS. 32 and 33, a one-piece tubular suture retainer is utilized to grip the left and right sections of the suture. Since the embodiment of the invention illustrated in FIGS. 32 and 33 is similar to the embodiment of the invention illustrated in FIGS. 29–31, similar terminology will be utilized to identify similar components. It should be understood that one or more of the features of the embodiments of the invention illustrated in FIGS. 1–31 could be used with the embodiment of the invention illustrated in FIG. 32.

In the embodiment of the invention illustrated in FIG. 32, a suture retainer 700 is formed from a single piece of a biodegradable polymeric material, such as polycaperlactone. The suture retainer 700 includes an annular flange or base 702 and an upright tubular cylindrical main section 704. The tubular cylindrical main section 704 is disposed in a coaxial relationship with the base 702. A straight cylindrical passage 706 extends through the tubular main section 704 and base 702 of the suture retainer 700. If desired, the passage 706 could have a nonlinear configuration.

Left and right sections 66 and 68 of the suture 52 are inserted through the passage 706 in the suture retainer 700. While a predetermined tension is maintained in the left and right sections 66 and 68 of the suture 52, a predetermined force, indicated schematically by the arrows 708 in FIG. 32, is applied to the main section 704 of the suture retainer. The force 708 is distributed over a relatively large surface area on the body tissue 54 by the base 702.

The suture retainer 700 is then plastically deformed to grip the left and right sections 66 and 68 of the suture 52. To plastically deform the suture retainer 700, force application members 712 and 714 are pressed against opposite sides of the main section 704 of the suture retainer 700 with a predetermined force, indicated schematically by the arrows 716 in FIG. 32. When the force 716 is applied to the suture retainer 700, the suture retainer is at a temperature below the transition temperature of the material forming the suture retainer. Therefore, the force 716 is effective to cause cold flow of the material of the suture retainer 700.

The force applied against the suture retainer 700 by the force applying members 712 and 714 is measured by a transducer or load cell 720. The magnitude of the force 716 is transmitted from the load cell 720 to a display unit 722. When a predetermined minimum force 716 has been applied to the suture retainer 700 for a predetermined minimum period of time by the force applying members 712 and 714, the display unit 722 activates an indicator 724.

The force applying members 712 and 714 are configured to form a plurality of bends 728 and 730 in the tubular main section 704 of the suture retainer 700 (FIG. 33). Thus, the force applying members 712 and 714 deform the main section 704 of the suture retainer 700 from a straight cylindrical configuration (FIG. 32) to a nonlinear configuration (FIG. 33). The bends 728 and 730, in combination with the cold plastic deformation of the material of the suture retainer 700, result in the suture retainer 700 having a firm grip on the left and right sections 66 and 68 of the suture 52. It should be understood that the force application members 712 and 714 could be configured to form a greater number of bends in the main section 704 of the suture retainer.

In the illustrated embodiment of the suture retainer 700, a single passage 706 (FIG. 32) extends through the suture retainer. If desired, a plurality of passages could be provided in the suture retainer 700. If this was done, the left section 66 of the suture would be inserted through one of the passages and the right section 68 would be inserted through another passage.

The bends 728 and 730 (FIG. 33) in the suture retainer 700 form smooth, continuous bends in the suture 52. This avoids the formation of stress concentrations in the suture 52. If a knot had been utilized in place of the suture retainer 700 to interconnect the sections 66 and 68 of he suture 52, stress concentrations would have been formed in the suture and the overall force transmitting capability of the suture would have been impaired.

The annular base 702 projects radially outward from the cylindrical main section. Sine the tension force transmitted to the suture retainer 700 by the suture 52 is transmitted to the body tissue 54 by the base 702, the suture tension force is transmitted to a relatively large surface area on the body tissue. This minimizes the possibility of the suture 52 and suture retainer 700 being pulled downward (as viewed in FIG. 33) into the body tissue 54 by the tension force in the suture. In addition, the large base 702 minimizes the possibility of damage to the body tissue 54.

If desired, a knot could be tied between the upper end portions of the sections 66 and 68 of the suture. This knot would be disposed above and would press against an upper (as viewed in FIG. 33) end of the suture retainer. Although stress concentrations would be formed in the suture 52 at the knot, the knot would not impair the force transmitting capability of the portion of the suture engaging the body tissue 54. This is because the suture retainer 700 would be disposed between the body tissue 54 and the knot.

Embodiment of FIG. 34

In the embodiment of the invention illustrated in FIG. 34, the suture retainer has a tubular configuration. Since the embodiment of the invention illustrated in FIG. 34 is similar to the embodiments of the invention illustrated in FIGS. 1–33, similar terminology will be utilized to identify similar components. It should be understood that one or more of the features of the embodiments of the invention illustrated in FIGS. 1–33 could be used with the embodiment of the invention illustrated in FIG. 34.

A suture 52 (FIG. 34) has left and right sections 66 and 68 which extend through a tubular cylindrical suture retainer 740 into body tissue 54. An apparatus 741 for pressing the suture retainer 740 against the body tissue 54 includes a tubular cylindrical plunger 742 having a cylindrical central passage 744 through which the left and right sections 66 and 68 of the suture 54 extends. The plunger 742 is enclosed in a tubular cylindrical housing 746.

The plunger 742 is pressed downward, relative to the housing 746 against the suture retainer 740 with a predetermined force, indicated by arrows 748 in FIG. 34. An annular transducer or load cell 750 provides an output indicative of the magnitude of the force 748 with which the suture retainer 740 is pressed against the body tissue 54 by the plunger 742.

While the left and right sections 66 and 68 of the suture 54 are being tensioned with a predetermined force and while the plunger 742 is being pressed against the suture retainer 740 with a predetermined force, the suture retainer 740 is plastically deformed. To plastically deform the suture retainer 740, a plurality of force applying or clamp members 754 and 756 are pressed against the suture retainer with a predetermined minimum force, indicated schematically by arrows 760 in FIG. 34. The force application members 754 and 756 may have an arcuate configuration to conform to the cylindrical configuration of the suture retainer 740 or may have a flat configuration. The force applied against the suture retainer 740 by the force 760 applying members 754 and 756 is sufficient to cause plastic deformation of the material of the suture retainer.

The force 760 is applied against the suture retainer while the suture retainer is at a temperature which is below the transition temperature of the biodegradable polymer which forms the suture retainer. Thus, the suture retainer is at approximately the same temperature as the body tissue 54 when the force 760 is applied against the suture retainer. The force 760 causes the material of the suture retainer to cold flow and grip the left and right sections 66 and 68 of the suture 54 in the manner previously explained.

Although the apparatus 741 has been illustrated in FIG. 34 in association with the suture retainer 740, it is contemplated that the apparatus 741 could be used with any one of the suture retainers of FIGS. 1–33. Although the force applying members 754 and 756 have an arcuate configuration to grip the arcuate outer side surface of the suture retainer 740. It is contemplated that the force applying members could have a different configuration to grip a suture retainer having a noncylindrical configuration.

Figure 35:
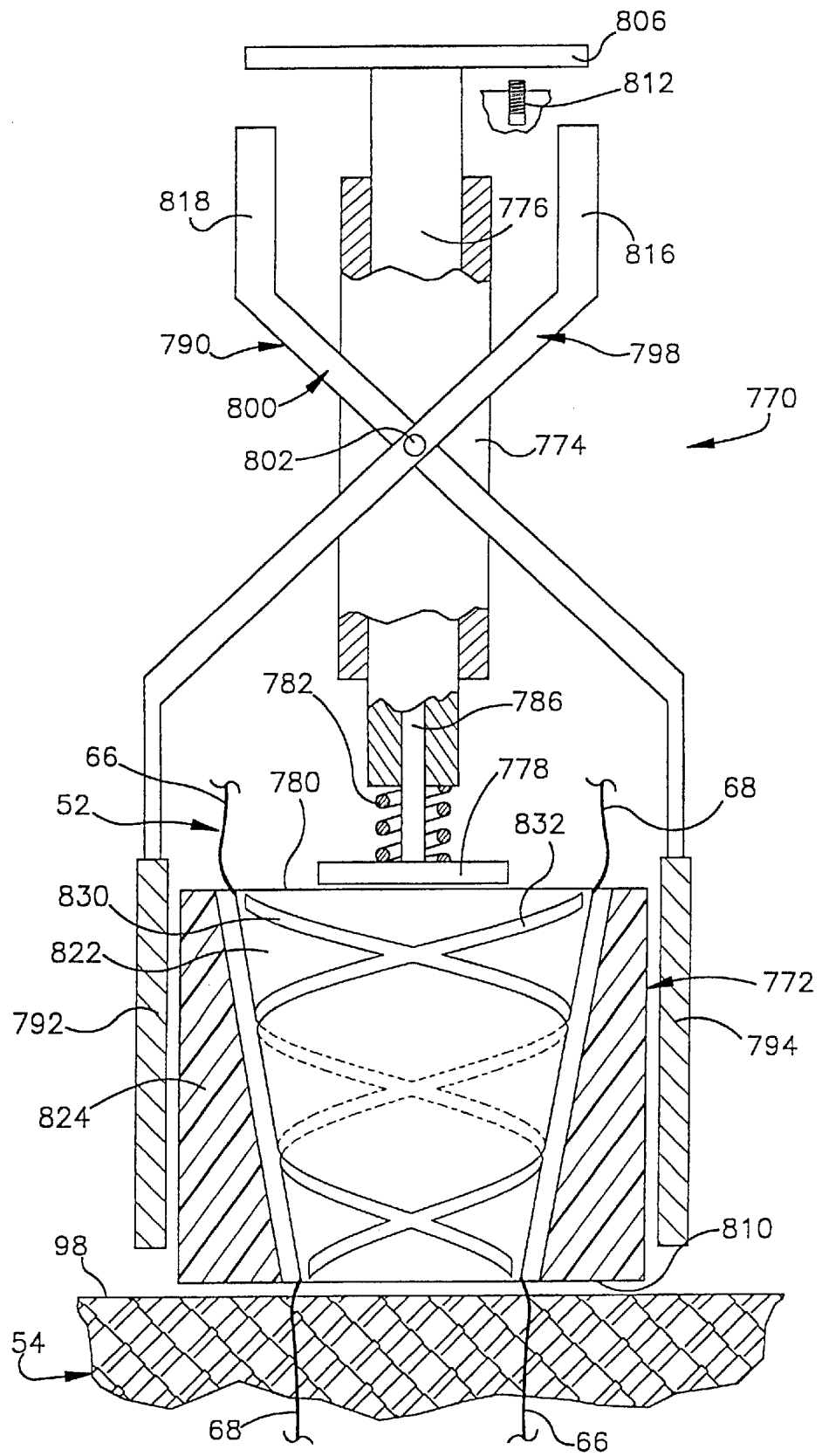
FIG. 35 is a schematic illustration of a tool which may be used to press the suture retainer of FIG. 13 against body tissue and to plastically deform the material of the suture retainer.

Embodiment of FIG. 35

In the embodiment of the invention illustrated in FIG. 35, an apparatus similar to the apparatus illustrated in FIG. 34 is utilized to install a suture retainer having the same construction as the suture retainer of FIGS. 13–16. Since the embodiment of the invention illustrated in FIG. 35 is similar to the embodiment of the invention illustrated in FIG. 34, similar terminology will be utilized to identify similar components.

An apparatus or tool 770 (FIG. 35) is utilized to position a suture retainer 772 relative to body tissue 54. The apparatus 770 includes a tubular housing or base 774 through which a cylindrical plunger 776 extends. A force application member 778 extends from the plunger 776 and is engageable with an upper or trailing end surface 780 of the suture retainer 772. A biasing spring 782 urges the force application member 778 to the extended position illustrated in FIG. 35.

Upon application of a predetermined force to the trailing end surface 780 of the suture retainer 772 by the force application member 778, an indicator connected with a shaft 786 indicates to an operator of the apparatus 770 that a desired force has been applied against the suture retainer 772. The indicator may be either a direct reading of the position of the shaft 786 relative to the plunger 776 or an output from a transducer, such as a load cell.

The apparatus 770 includes a gripper assembly 790 which is operable to grip and to deform the suture retainer 772. The gripper assembly 790 includes a left force application member 792 and a right force application member 794. The force application members 792 and 794 engage opposite sides of the suture retainer 772. The force application members 792 and 794 are configured to correspond to the shape of an outer side surface of the suture retainer 772.

An actuator member 798 is connected with the left force application member 792. A second actuator member 800 is connected with the right force application member 794. The actuator members 798 and 800 are pivotally mounted on the housing 774 at a pivot connection indicated schematically at 802 in FIG. 35.

Downward force is manually applied to an upper input end portion 806 of the plunger 776 while a predetermined tension is maintained in the left and right sections 66 and 68 of the suture 52. The downward (as viewed in FIG. 35) force applied against the plunger 776 is transmitted through the spring 782 to the force application member 778. The force application member 778 applies force to the trailing end surface 780 of the suture retainer 772 to press a leading end surface 810 on the suture retainer 772 against the side surface 98 of the body tissue 54.

An adjustable stop member 812 is connected with the housing 774. The stop member 812 is adjustable to limit the extent of downward movement of the input end portion 806 of the plunger 776 relative to the housing 774. This enables the stop member 812 to limit the amount of force transmitted through the spring 782 to the suture retainer 772 to a predetermined force.

Manual force is applied against upper (as viewed in FIG. 35) end portions 816 and 818 of the actuator members 798 and 800. During the application of the manual force to the upper end portions 816 and 818 of the actuator members 798 and 880, the predetermined tension is maintained in the left and right sections 66 and 68 of the suture 52. In addition, the predetermined downward force is transmitted from the plunger 776 through the spring 782 and force application member 778 to the suture retainer 772.

The manual force applied to the end portions 816 and 818 of the actuator members 798 and 800 is transmitted to the force application members 792 and 794. The force application members 792 and 794 are pressed against the suture retainer 792 with sufficient force too plastically deform the suture retainer by cold flowing the material of the suture retainer.

Although the suture retainer 772 may have any one of the constructions illustrated in FIGS. 1–34, the suture retainer 772 has the same construction as the suture retainer 244 of FIG. 13. Thus, the suture retainer 772 includes a conical body 822 and a cylindrical sleeve 824. The suture 52 has a left section 66 which is wrapped for a plurality of turns around the conical body 822 and is disposed in a helical groove 830 formed in the conical body 822. Similarly, a right section 68 of the suture 52 is wrapped for a plurality of turns around the conical body 822 and is disposed in a helical groove 832 formed in the conical body 822.

When the suture retainer 772 is to be positioned relative to the body tissue 54, the suture 52 is inserted through the sleeve 824. The left section 66 of the suture is then positioned in the helical groove 830 in the conical body 822 of the suture retainer 772. The right section 68 of the suture 52 is positioned in the helical groove 832 in the conical body 822 of the suture retainer 772.

The apparatus or tool 770 is then operated to hold the suture retainer 772 in the manner illustrated schematically in FIG. 35. Thus, the force application member 778 is positioned in abutting engagement with the trailing end surface 780 of the suture retainer 772. At the same time, the left and right force application members 792 and 794 grip the sleeve 824 of the suture retainer 772. This results in the conical body 822 of the suture retainer 772 being telescopically pressed into the sleeve 824 while the sleeve is held by the force application members 792 and 794.

While the predetermined tension is maintained in the left and right sections 66 and 68 of the suture 52, the tool 770 and the suture retainer 772 are moved along the suture 52 toward the body tissue 54. The tool 770 is moved along a path which extends parallel to the taut portions of the left and right sections 66 and 68 of the suture 52 which extend upward (as viewed in FIG. 35) from the suture retainer 772. As the suture retainer 772 is moved along the suture 52 toward the body tissue 54, the left and right sections 66 and 68 of the suture slide along the grooves 830 and 832. The grooves 830 and 832 are effective to maintain the helical turns or loops in the left and right sections 66 and 68 of the suture 52 as the suture retainer 772 moves along the suture 52 toward the body tissue 54.

The force required to slide the suture retainer 772 along the suture 52 is transmitted from the tool 700 to the suture retainer. Thus, force is transmitted from the force application member 778 to the trailing end surface 780 of the conical body 822. At the same time, a clamping force is transmitted from the force application members 792 and 794 to the sleeve 824. The sleeve 824 is securely held by the force application members 792 and 794 while the conical body 822 is pressed axially against the sleeve by the force application member 778. During movement of the suture retainer 772 along the suture 52, the force applied against the suture retainer by the tool 700 is ineffective to cause significant deformation of the suture retainer.

At this time, the tool 770 extends along the portions of the left and right sections 66 and 68 of the suture 52 extending upward (as viewed in FIG. 35) from the suture retainer 772. Since the tool 770 extends from the suture retainer 772 in the same direction as the left and right sections 66 and 68 of the suture 52, the tool can be used to position the suture retainer relative to body tissue 54 in very restricted space commonly present in operating environments.

When the leading end surface 810 on the suture retainer 772 engages the upper (as viewed in FIG. 35) side surface 98 of the body tissue 54 (FIG. 35), the force applied against the actuator members 798 and 800 is reduced. Manual force is then applied against the input end portion 806 of the plunger 776 to move the plunger downward and compress the spring 782. The stop member 812 is engaged by the input end portion 806 of the plunger 776 when a predetermined force is being transmitted through the spring 782 and force application member 778 to the suture retainer 772.

This results in the predetermined downward force being transmitted from the force application member 778 to the suture retainer 772 to press the conical body against the sleeve 824. The predetermined downward force is then transmitted from the sleeve 824 and conical body 822 to the body tissue 54. While the suture retainer 772 is being pressed against the body tissue with the predetermined downward force, a predetermined tension force is maintained in the left and right sections 66 and 68 of the suture 52.

In the schematic illustration of FIG. 35, there is space between the conical body 822 and the sleeve 824. In addition, there is space between the sleeve 824 and the force application members 792 and 794. It should be understood that the conical outer side surface of the body 822 is pressed firmly against the correspondingly shaped conical inner side surface of the sleeve 824. It should also be understood hat the force application members 792 and 794 are pressed against the cylindrical outer side surface of the sleeve 824. At this time, the left and right sections 66 and 68 of the suture are tensioned.

While the predetermined force is being applied against the trailing end surface 780 of the suture retainer 772 by the force application member 778, manual force is applied against the upper end portions 816 and 818 of the actuator members 798 and 800 to effect plastic deformation of the suture retainer 772. Thus, the left and right force applying members 792 and 794 are pressed against the cylindrical sleeve 824 with sufficient force to plastically deform both the cylindrical sleeve and the conical body 822 of the suture retainer 772. At this time, the suture retainer 772 is at approximately the same temperature as the body tissue 54 and is at a temperature which is below the transition temperature of the biodegradable polymeric material forming the suture retainer. Therefore, cold flowing the material of the suture retainer occurs under the influence of the force applied against the suture retainer 772 by the left and right force applying members 792 and 794.

The cold flowing of the material of the suture retainer 772 under the influence of the force applied to the suture retainer by the force application members 792 and 794 results in the suture 52 being firmly gripped in the manner set forth in association with the suture retainer 244 of the embodiment of FIGS. 13–16. The application of force to the actuator members 798 and 800 is then interrupted. The application of force to the input end portion 806 of the plunger 776 is also interrupted. The apparatus 770 is then moved upward (as viewed in FIG. 35) away from the suture retainer.

Although the apparatus 770 has been disclosed herein in association with the suture retainer 772, it is contemplated that the apparatus could be utilized to install suture retainers having a different construction. If the apparatus 770 is used to install a suture retainer having an outer side surface with a configuration which is different than the configuration of outer side surface of the suture retainer 772, the configuration of the force application members 792 and 794 would be modified to correspond to the configuration of the suture retainer to be installed. For example, if the suture retainer had a flat outer side surface, the force application members 792 and 794 would be modified to have flat surfaces to engage the suture retainer. If the suture retainer had the spherical outer side surface of the suture retainer 50 (FIG. 2), the force application members 792 and 794 would have configurations corresponding to the configuration of portions of a sphere.

Figure 36:
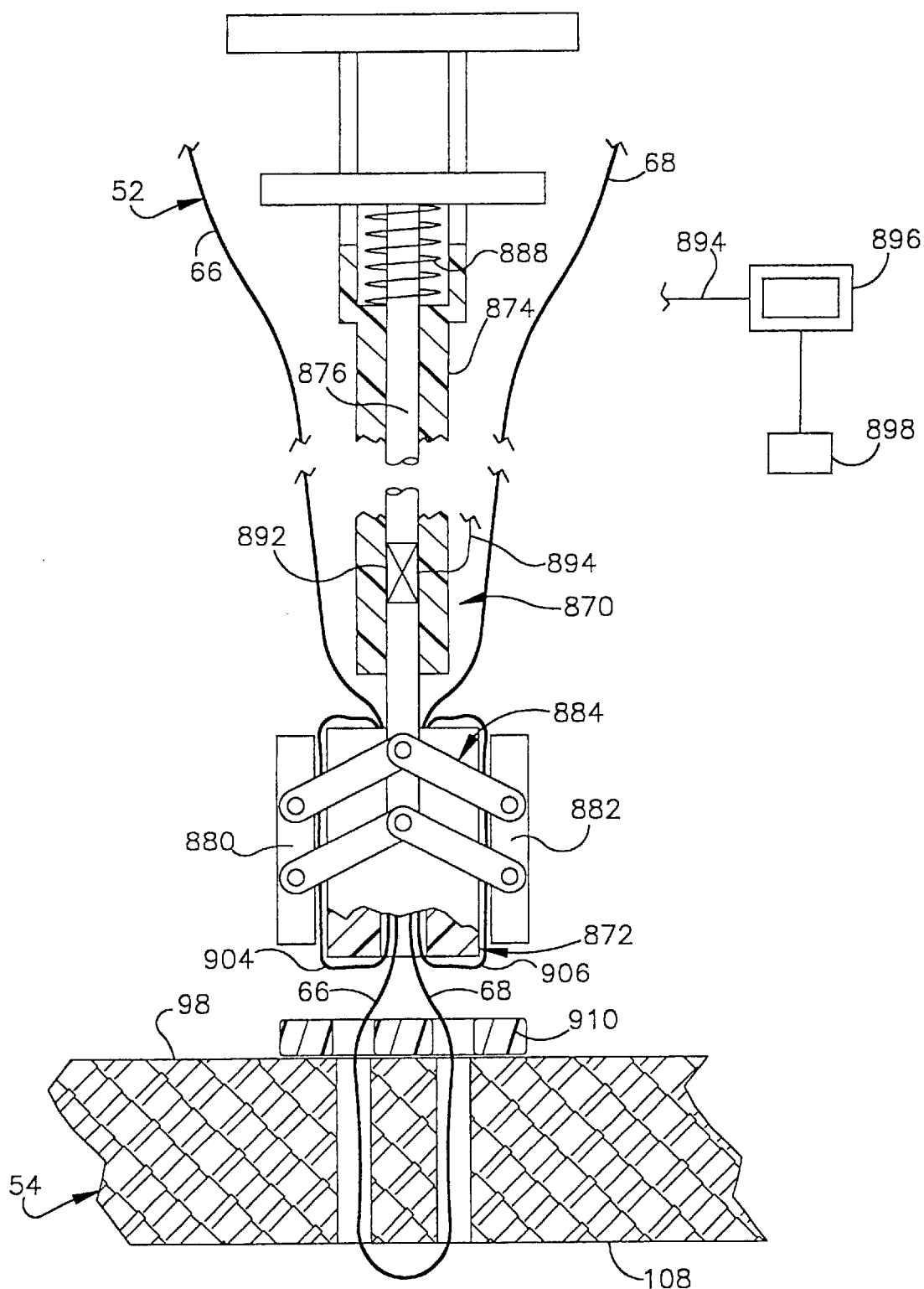
FIG. 36 is a schematic illustration of another embodiment of a tool which may be used to press a suture retainer against body tissue and to plastically deform the material of the suture retainer.

Embodiment of the Invention Illustrated in FIG. 36

In the embodiment of the invention illustrated in FIG. 35, an apparatus 770 for installing a suture retainer 772 is disclosed. In the embodiment of the invention illustrated in FIG. 36, a second apparatus for installing a suture retainer is disclosed. Since the embodiment of the invention illustrated in FIG. 36 is similar to the embodiment of the invention illustrated in FIG. 35, similar terminology will be utilized to identify similar components.

An apparatus or tool 870 for positioning a suture retainer 872 relative to body tissue 54 includes a base or housing 874. A cylindrical plunger 876 is slidable in the housing 874. The plunger 876 is connected with left and right force application or clamp members 880 and 882 by a pair of linkages 884. Although only one of the linkages 884 has been shown in FIG. 36, it should be understood that there is a second linkage having the same construction as the linkage 884 connected with the plunger 876.

A biasing spring 888 extends around the plunger 876 and urges the plunger upward (as viewed in FIG. 36). The force transmitted from the biasing spring 888 through the plunger 876 and linkages 884 urges the left and right force application members 880 and 882 into engagement with the suture retainer 872. The force provided by the spring 888 is insufficient to cause significant deformation of the suture retainer 872. However, the force provided by the spring 888 is sufficient to enable the force application members 880 and 882 to hold the suture retainer 872 during sliding of the suture retainer along the suture 52.

A transducer or load cell 892 is connected with the plunger 876 and provides an output signal, over a lead 894 to a display unit 896. This output is indicative of the magnitude of the force transmitted through the plunger 876. When a predetermined force has been applied by the force application members 880 and 882 against the suture retainer 872 for a predetermined minimum length of time, an indicator 898 is activated by the display unit 896.

The specific suture retainer 872 illustrated in FIG. 36 has a one-piece tubular cylindrical construction. The suture 52 has left and right sections 66 and 68 which are wrapped around the suture retainer 872 in the same manner as in which the suture 52 is wrapped around the suture retainer 50 of FIG. 2. Thus, a loop 904 is formed in the left section 66 of the suture 52 and extends around a portion of the tubular cylindrical suture retainer 872. Similarly, a loop 906 is formed in the right section 68 of the suture 52 and extends around a portion of the tubular cylindrical suture retainer 872.

In the embodiment of the invention illustrated in FIG. 36, a force distribution member or button 910 is provided at the upper side surface 98 of the body tissue 54. The force transmission member or button 910 distributes the force applied by the suture retainer 872 to the body tissue 54 over a relatively large area on the body tissue. If desired, a second force distribution member could be provided between the suture and a lower side surface 108 of the body tissue 54. Since the suture retainer 872 is effective to apply force to a relatively large area, the button 910 may be omitted if desired.

When the suture retainer 872 is to be installed in the body tissue, the two sections 66 and 68 of the suture are sewn through the body tissue 54 and are then inserted into the suture retainer 872. During insertion of the left and right sections 66 and 68 of the suture 52 into the suture retainer 872, the loops 904 and 906 are formed in the two sections 66 and 68 of the suture.

The plunger 876 is then manually moved downward in the housing 874 against the influence of the biasing spring 888 to move the force application members 880 and 882 apart. When the force application members 880 and 882 have been positioned adjacent to opposite sides of the suture retainer 872, the downward force applied against the plunger 876 is released. This results in the biasing spring 888 moving the plunger 876 upward to actuate the linkages 884 to press the force application members 880 and 882 against opposite sides of the suture retainer 874.

The left and right sections 66 and 68 of the suture 52 are then tensioned. The apparatus or tool 870 is then moved along the left and right sections 66 and 68 of the suture 52 toward the body tissue. As this occurs, the loops 904 and 906 are displaced downwardly along the tensioned sections 66 and 68 of the suture 52 toward the body tissue. During downward displacement of the loops 904 and 906 toward the body tissue 54, the left and right sections 66 and 68 of the suture 52 slide along surfaces on the suture retainer 872.

After the suture retainer 872 has been moved into engagement with the button or force distribution member 910, the leading end of the suture retainer 872 is pressed against the button with a predetermined force. This force is transmitted through the plunger 876 and is measured by the transducer 892. Once the suture retainer 872 has been pressed against the button or force distribution member 910 with a predetermined force, the plunger 876 is manually pulled upward relative to the housing 874. This results in the transmission of force through the linkage 884 to the force applying members 880 and 882.

The force applying members 880 and 882 apply sufficient force to the suture retainer 872 to effect plastic deformation of the suture retainer. At this time, the suture retainer is at a temperature below the transition temperature of the biodegradable polymeric material of the suture retainer. Thus, the suture retainer is at a temperature which is the same as the temperature of the body tissue 54. The plastic deformation of the suture retainer 872 results in cold flowing of the material of the suture retainer and gripping of the left and right sections 66 and 68 of the suture 52 in the manner previously explained in conjunction with the embodiments of the invention illustrated in FIGS. 1–35.

It should be understood that the tool 870 may be used to install any of the suture retainers illustrated in FIGS. 1–33. Of course, the force application or clamp members 880 and 882 would be configured so as to grip the outer side surface of the specific suture retainer with which the tool is to be used.

Conclusion

The present invention provides a new and improved method and apparatus for use in securing a suture 52 relative to body tissue 54. A suture retainer 50 ((FIGS. 1–3) may be plastically deformed to grip the suture. The plastic deformation of the suture retainer 50 may include pressing the material of the suture retainer against the suture 52 by cold flowing material of the suture retainer. The plastic deformation of the material of the suture retainer 50 may be performed while transmitting a predetermined force from the suture retainer 50 to the body tissue 54.

The strength of a connection between the suture retainer 50 and the suture 52 may be increased by forming bends 72, 74, 76 and 78 in the suture 52 before deforming the material of the suture retainer 50. As the suture retainer is moved along the first and second sections of the suture toward the body tissue 54, the bends 72, 74, 76 and 78 are moved along the suture with the suture retainer. The bends 72, 74, 76, and 78 may be formed by wrapping the suture 52 around a circular portion of the suture retainer (FIGS. 9, 13, 17, and 20), by moving the suture through one or more passages in the suture retainer (FIGS. 2, 21, 23, 24, 25, 26, and 29), by bending the suture around a member (FIG. 6), and/or by deflecting a portion of the suture retainer through which the suture extends (FIG. 32).

The suture retainer 50 may be gripped with a tool 770 or 870 which is moved along the suture 52 to move the suture retainer toward the body tissue 54. The tool 770 or 870 may be used to urge the suture retainer toward the body tissue with a predetermined minimum force. In addition, the tool 770 or 870 may be used to plastically deform the material of the suture retainer when the suture retainer has been moved to a desired position. The tool 770 or 870 may be used in association with any of the embodiments of the suture retainer illustrated in FIGS. 1–33.

It should be understood that the specific and presently preferred embodiments of the invention illustrated herein are only examples of many different embodiments of the invention which are possible. In describing the presently preferred embodiments of the invention illustrated herein, similar terminology has been used to designate components which are similar in structure and function. The specific features of any one embodiment of the invention may be utilized in association with any of the other embodiments of the invention.

Having described the invention, the following is claimed:

1. A method of securing a suture relative to body tissue, said method comprising the steps of providing a suture retainer having an outer surface which extends between first and second end portions of the suture retainer and a groove which extends inward from the outer surface and extends through a plurality of turns around a portion of the suture retainer, positioning a portion of the suture in the groove with the portion of the suture extending through a plurality of turns around a portion of the suture retainer, and gripping the suture by deforming the suture retainer with the portion of the suture disposed in the groove.

2. A method as set forth in claim 1 wherein said groove has a helical configuration, said step of positioning a portion of the suture in the groove includes imparting a helical configuration to the portion of the suture disposed in the groove.

3. A method as set forth in claim 1 wherein said step of gripping the suture by deforming the suture retainer includes cold flowing material of the suture retainer.

4. A method as set forth in claim 1 wherein said step of gripping the suture by de forming the suture retainer includes deflecting a portion of the material of the suture retainer to at least partially close an opening to the groove.

5. A method as set forth in claim 1 wherein said step of positioning a portion of the suture in the groove includes positioning first and second sections of the suture in the groove in a side-by-side relationship, said step of gripping the suture by deforming the suture retainer includes gripping the first and second sections of the suture.

6. A method as set forth in claim 1 further including the steps of tensioning the suture and transmitting force from the suture retainer to the body tissue prior to performing said step of gripping the suture by deforming the suture retainer.

7. A method as set forth in claim 1 further including the step of moving the suture retainer along the suture toward the body tissue prior to performing said step of gripping the suture by deforming the suture retainer and after performing said step of positioning a portion of the suture in the groove.

8. A method of securing a suture relative to body tissue, said method comprising the steps of providing a suture retainer having a groove which extends around the suture retainer, positioning a portion of the suture in the groove with the suture extending around the suture retainer, and gripping the suture by deforming the suture retainer with a portion of the suture disposed in the groove and extending around the suture retainer.

9. A method as set forth in claim 8 wherein said groove has a helical configuration, said step of positioning a portion of the suture in the groove includes imparting a helical configuration to the portion of the suture disposed in the groove.

10. A method as set forth in claim 8 wherein said step of gripping the suture by deforming the suture retainer includes cold flowing material of the suture retainer.

11. A method as set forth in claim 8 wherein said step of gripping the suture by deforming the suture retainer includes deflecting a portion of the material of the suture retainer to at least partially close an opening to the groove.

12. A method as set forth in claim 8 wherein said step of positioning a portion of the suture in the groove includes positioning first and second sections of the suture in the groove in a side-by-side relationship, said step of gripping the suture by deforming the suture retainer includes gripping the first and second sections of the suture.

13. A method as set forth in claim 8 further including the steps of tensioning the suture and transmitting force from the suture retainer to the body tissue prior to performing said step of gripping the suture by deforming the suture retainer.

14. A method as set forth in claim 8 further including the step of moving the suture retainer along the suture toward the body tissue prior to performing said step of gripping the suture by deforming the suture retainer and after performing said step of positioning a portion of the suture in the groove.

15. A method of securing a suture relative to body tissue, said method comprising the steps of providing a suture retainer having a first groove and a second groove which intersects the first groove, positioning a first portion of the suture in the first groove, positioning a second portion of the suture in the second groove with the second portion of the suture extending across the first portion of the suture where the second groove intersects the first groove, and gripping the suture by deforming the suture retainer with the first portion of the suture in the first groove and the second portion of the suture in the second groove.

16. A method as set forth in claim 15 wherein the first groove extends through a plurality of turns around the suture retainer and the second groove extends for a plurality of turns around the suture retainer, said step of positioning a first portion of the suture in the first groove includes positioning the first portion of the suture in the first groove with the first portion of the suture extending for a plurality of turns around the suture retainer, said step of positioning the second portion of the suture of the suture in the second groove includes positioning the second portion of the suture in the second groove with the second portion of the suture extending for a plurality of turns around the suture retainer.

17. A method as set forth in claim 15 wherein the first groove has a helical configuration and the second groove has a helical configuration, said step of positioning a first portion of the suture in the first groove includes imparting a helical configuration to the portion of the suture disposed in the first groove, said step of positioning a second portion of the suture in the second groove includes imparting a helical configuration to the portion of the suture disposed in the second groove.

18. A method as set forth in claim 15 wherein said step of gripping the suture by deforming the suture retainer includes cold flowing material of the suture retainer.

19. A method as set forth in claim 15 wherein said step of gripping the suture by deforming the suture retainer includes deflecting a portion of the material forming the suture retainer to at least partially close an opening to the first groove and to at least partially close an opening to the second groove.

20. A method as set forth in claim 15 further including the steps of tensioning the suture and transmitting force from the suture retainer to the body tissue prior to performing said step of gripping the suture by deforming the suture retainer.

21. A method as set forth in claim 15 further including the step of moving the suture retainer along the suture toward the body tissue prior to performing said step of gripping the suture by deforming the suture retainer and after performing said steps of positioning the first portion of the suture in the first groove and positioning the second portion of the suture in the second groove.

22. A method as set forth in claim 15 wherein said step of gripping the suture by deforming the suture retainer includes pressing material of the suture retainer against the suture at a location where the second portion of the suture extends across the first portion of the suture.

23. A method as set forth in claim 15 wherein the first groove extends at least part way around the suture retainer in a first direction and the second groove extends at least part way around the suture retainer in a second direction, said steps of positioning a first portion of the suture in the first groove and positioning the second portion of the suture in the second groove includes wrapping the first portion of the suture at least part way around the suture retainer in one direction and wrapping the second portion of the suture at least part way around the suture retainer in another direction.

24. A method of securing a suture relative to body tissue, said method comprising the steps of providing a suture retainer having a groove with a bottom which extends around the suture retainer and is offset along a central axis of the suture retainer from an opening to the groove which extends around the suture retainer, moving a portion of the suture into the groove to a position in which the portion of the suture is disposed adjacent to the bottom of the groove and is offset along the central axis of suture retainer from the opening to the groove, and closing the opening to the groove with the portion of the suture disposed adjacent to the bottom of the groove, said step of closing the opening to the groove includes deforming material of the suture retainer to block the opening.

25. A method as set forth in claim 24 wherein said step of closing the opening to the groove is performed with the portion of the suture disposed in the groove extending along the groove for the extent of the groove.

26. A method as set forth in claim 24 wherein said step of closing the opening to the groove is performed with the portion of the suture disposed in the groove extending for more than one complete turn around the suture retainer.

27. A method as set forth in claim 24 wherein said groove has a helical configuration, said step of moving a portion of the suture into the groove includes imparting a helical configuration to the portion of the suture disposed in the groove.

28. A method as set forth in claim 24 wherein said step of closing the opening to the groove by deforming the suture retainer includes cold flowing material of the suture retainer.

29. A method as set forth in claim 24 wherein said step of closing the opening to the groove by deforming material of the suture retainer includes gripping the portion of the suture disposed in the groove with the material of the suture retainer.

30. A method as set forth in claim 24 wherein said step of positioning a portion of the suture in the groove includes positioning first and second sections of the suture in the groove in a side-by-side relationship.

31. A method as set forth in claim 24 further including the steps of tensioning the suture and transmitting force from the suture retainer to the body tissue prior to performing said step of closing the opening to the groove.

32. A method as set forth in claim 24 further including the step of moving the suture retainer along the suture toward the body tissue prior to performing said step of closing the opening to the groove and after performing said step of positioning a portion of the suture in the groove.

* * * * *